United States Patent [19]
Ross et al.

[11] Patent Number: 5,389,659
[45] Date of Patent: Feb. 14, 1995

[54] C-LINKED PYRAZOLE DERIVATIVES

[75] Inventors: Barry C. Ross, Luton; David Middlemiss, Bishops Stortford; Colin D. Eldred, Ware; John G. Montana, Ware; Pritom Shah, Ware, all of England

[73] Assignee: Glaxo Group Limited, London, England

[21] Appl. No.: 666,746

[22] Filed: Mar. 8, 1991

[30] Foreign Application Priority Data

Mar. 9, 1990 [GB] United Kingdom ............... 9005354

[51] Int. Cl.⁶ ............... A61K 31/41; C07D 403/10
[52] U.S. Cl. ............... 514/381; 514/406; 548/253; 548/376.1
[58] Field of Search ............... 548/253; 514/381

[56] References Cited
FOREIGN PATENT DOCUMENTS
323841 12/1984 European Pat. Off. .

*Primary Examiner*—Robert W. Ramsuer
*Attorney, Agent, or Firm*—Bacon & Thomas

[57] ABSTRACT

The invention provides compounds of the general formula (I):

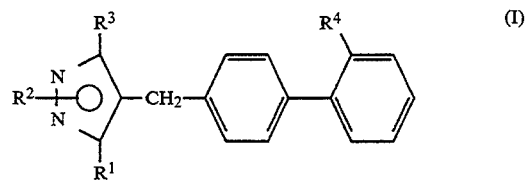

or a physiologically acceptable salt, solvate (e.g. hydrate) or a metabolically labile ester thereof.

The compounds may be used in the treatment or prophylaxis of hypertension and diseases associated with cognitive disorders.

40 Claims, No Drawings

C-LINKED PYRAZOLE DERIVATIVES

This invention relates to C-linked pyrazole derivatives, processes for their preparation and pharmaceutical compositions containing them. According to the invention we provide a compound of general formula (I):

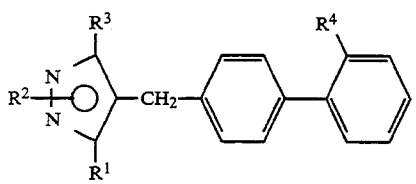

or a physiologically acceptable salt, solvate (e.g. hydrate) or a metabolically labile ester thereof in which $R^1$ represents a hydrogen atom or a group selected from $C_{1-6}$alkyl or $C_{2-6}$alkenyl;

$R^2$ represents a hydrogen atom or a group selected from $C_{1-6}$alkyl, $C_{3-7}$cycloalkyl, $C_{3-7}$cycloalkyl $C_{1-4}$alkyl, $C_{3-6}$alkenyl, fluoro$C_{1-6}$alkyl, fluoro$C_{3-6}$alkenyl, phenyl, —$(CH_2)_kCOR^5$ or —$(CH_2)_kSO_2R^5$;

$R^3$ represents a hydrogen atom or a group selected from $C_{1-6}$alkyl optionally substituted by a hydroxy or $C_{1-6}$alkoxy group, $C_{2-6}$alkenyl, fluoro$C_{1-6}$alkyl, —$(CH_2)_mR^6$, —$(CH_2)_nCOR^7$ or —$(CH_2)_pNR^8COR^9$;

$R^4$ represents a group selected from —$CO_2H$, —$NHSO_2CF_3$ or a C-linked tetrazolyl group;

$R^5$ represents a group selected from $C_{1-6}$alkyl, $C_{2-6}$alkenyl, $C_{1-6}$alkoxy or the group —$NR^{10}R^{11}$;

$R^6$ represents a phenoxy or benzyloxy group;

$R^7$ represents a hydrogen atom or a group selected from hydroxy, $C_{1-6}$alkyl, $C_{1-6}$alkoxy, phenyl, phenoxy or the group —$NR^{10}R^{11}$;

$R^8$ represents a hydrogen atom or a $C_{1-6}$alkyl group;

$R^9$ represents a hydrogen atom or a group selected from $C_{1-6}$alkyl, $C_{1-6}$alkoxy, phenyl, benzyl, phenoxy or the group —$NR^{10}R^{11}$;

$R^{10}$ and $R^{11}$ which may be the same or different each independently represent a hydrogen atom or a $C_{1-4}$alkyl group or —$NR^{10}R^{11}$ forms a saturated heterocyclic ring which has 5 or 6 ring members and may optionally contain in the ring one oxygen atom;

k represents zero or an integer from 1 to 4, preferably zero, 1 or 2, especially zero or 1;

m represents an integer from 1 to 4, preferably 1 or 2, especially 1;

n represents zero or an integer from 1 to 4, preferably zero, 1 or 2, especially 0 or 1; and p represents an integer from 1 to 4, preferably 1 or 2.

Where the compound of general formula (I) is optically active, said formula (I) is intended to cover all enantiomers, diastereoisomers and mixtures thereof including racemates. Where a compound of the present invention contains one or two double bonds, these may exist in the cis or trans configuration. Furthermore where such geometric isomers exist, formula (I) is intended to cover mixtures thereof.

The invention also includes within its scope the solvates, especially the hydrates, of compounds of general formula (I).

Within the above definition the term 'alkyl' or 'alkoxy' as a group or part of a group means that the group is straight or branched. The term 'alkenyl' as a group or part of a group means that the group is straight or branched and contains at least one carbon-carbon double bond. The term 'cycloalkyl' as a group or part of a group may be, for example, a cyclopropyl, cyclobutyl, cyclopentyl or cyclohexyl group.

The term 'fluoro$C_{1-6}$alkyl' or 'fluoro$C_{3-6}$alkenyl' means an alkyl or alkenyl group in which one or more hydrogen atoms have been substituted by a fluorine atom, for example, —$CH_2CF_3$ or —$CH=CHCF_3$.

Within the above definition when —$NR^{10}R^{11}$ represents a saturated heterocyclic ring, this contains 5 or 6 ring members, one of which may be an oxygen atom. Suitable heterocyclic groups are a pyrrolidino, piperidino or morpholino group.

A preferred class of compounds of general formula (I) is that wherein the group $R^1$ is a $C_{1-5}$alkyl (for example, ethyl, n-propyl or n-butyl), especially a $C_{3-5}$alkyl, or $C_{3-5}$alkenyl group. Particularly preferred are those compounds wherein $R^1$ is an n-butyl, n-propyl, but-1-enyl or prop-1-enyl group.

Another preferred class of compounds of general formula (I) is that wherein the group $R^2$ is a fluoro$C_{1-6}$alkyl group or the group $(CH_2)_kSO_2R^5$. Particularly preferred are those compounds wherein $R^2$ represents a fluoro$C_{1-3}$alkyl group, especially —$CH_2CF_3$, or $R^5$ represents the group —$NR^{10}R^{11}$ (where $R^{10}$ and $R^{11}$ each represent a $C_{1-4}$alkyl group), especially $SO_2N(CH_3)_2$.

A further preferred class of compound of general formula (I) is that wherein the group $R^2$ is a group selected from $C_{1-6}$alkyl, preferably $C_{1-5}$alkyl, especially ethyl, isopropyl or isobutyl; $C_{3-7}$cycloalkyl, preferably $C_{3-5}$cycloalkyl, especially cyclobutyl; $C_{3-7}$cycloalkyl$C_{1-4}$alkyl, preferably $C_{3-5}$cycloalkyl$C_{1-4}$alkyl, especially cyclopropylmethyl; or phenyl.

Another preferred class of compound of general formula (I) is that wherein the group $R^2$ is adjacent to the group $R^3$.

Yet another preferred class of compounds of general formula (I) is that wherein $R^3$ is selected from a hydrogen atom or a group selected from $C_{1-6}$alkyl, preferably $C_{1-3}$alkyl, optionally substituted by hydroxy or $C_{1-3}$alkoxy, especially methoxy; or —$(CH_2)_mR^6$, especially wherein $R^6$ is a benzyloxy group; or —$(CH_2)_nCOR^7$ especially wherein $R^7$ represents hydrogen hydroxy or $C_{1-3}$alkoxy, especially methoxy, and m is 1 or 2 and n is zero, 1 or 2, especially zero or 1. In particular, $R^3$ may represent a hydrogen atom or a group selected from methyl, ethyl, propyl, butyl,—$CH_2OH$, —$CHO$, —$CH_2OCH_3$ or —$CO_2H$.

Another preferred class of compounds of general formula (I) is that wherein $R^3$ is the group —$(CH_2)_pNR^8COR^9$, especially wherein $R^8$ represents hydrogen or a $C_{1-3}$alkyl group and $R^9$ represents hydrogen or a $C_{1-3}$alkyl or $C_{1-3}$alkoxy group.

Preferably, in the compounds of general formula (I), $R^4$ may be the group —$CO_2H$, or a C-linked tetrazolyl group.

Particularly preferred compounds are:

4'-[[3-butyl-5-(methoxymethyl)-1-(2,2,2-trifluoroethyl)-1H-pyrazol-4-yl]methyl][1,1'-biphenyl]-2-carboxylic acid;

4'-[[5-butyl-3-(methoxymethyl)-1-(2,2,2-trifluoroethyl)-1H-pyrazol-4-yl]methyl][1,1'-biphenyl]-2-carboxylic acid;

5-[4'-[[3-butyl-5-(methoxymethyl)-1-(2,2,2-trifluoroethyl)-1H-pyrazol-4-yl]methyl][1,1'-biphenyl]-2-yl]-1H-tetrazole;

5-[4'[[5-butyl-3-(methoxymethyl)-1-(2,2,2-trifluoroethyl)-1H-pyrazol-4-yl]methyl][1,1'-biphenyl]-2-yl]-1H-tetrazole;

4'-[[5-butyl-1-[(dimethylamino)sulphonyl]-3-(methoxymethyl)-1H-pyrazol-4-yl]methyl][1,1'-biphenyl]-2-carboxylic acid;

4'-[[3-butyl-1-[(dimethylamino)sulphonyl]-5-(methoxymethyl)-1H-pyrazol-4-yl]methyl][1,1'-biphenyl]-2-carboxylic acid;

5-[4'-[[3-butyl-1-[(dimethylamino)sulphonyl]-5-(methoxymethyl)-1H-pyrazol-4-yl]methyl][1,1'-biphenyl]-2-yl]-1H-tetrazole;

5-[4'-[[5-butyl-1-[(dimethylamino)sulphonyl]-3-(methoxymethyl)-1H-pyrazol-4-yl]methyl][1,1'-biphenyl]-2-yl]-1H-tetrazole; and the physiologically acceptable salts, solvates and metabolically labile esters thereof.

Further particularly preferred compounds of the present invention include:

3-butyl-1-ethyl-4-[[2'-(1H-tetrazol-5-yl) [1,1'-biphenyl]-4-yl ]methyl]-1H-pyrazole-5-methanol;

3-butyl-1-(1-methylethyl)-4-[[2'-(1H-tetrazol-5-yl) [1,1'-biphenyl ]-4-yl]methyl]-1H-pyrazole-5-methanol;

3-butyl-1-(2-methylpropyl)-4-[[2'-(1H-tetrazol-5-yl) [1,1'-biphenyl ]-4-yl]methyl]-1H-pyrazole-5-methanol;

3-butyl-1-(2-cyclopropylmethyl)-4-[[2'-(1H-tetrazol-5-yl) [1,1'-biphenyl]-4-yl]methyl]-1H-pyrazole-5-methanol;

3-butyl-1-cyclobutyl-4-[[2'-( 1H-tet razol-5-yl ) [1,1'-biphenyl]-4-yl]methyl]-1H-pyrazole-5-methanol;

1,3-dibutyl-4-[[2'-(1H-tetrazol-5-yl) [t, 1'-biphenyl]-4-yl ]methyl]-1H-pyrazole-5 -methanol;

1-ethyl-3-propyl-4-[[2'-(1H-tetrazol-5-yl) [1,1'-biphenyl]-4-yl ]methyl]-1H-pyrazole-5-methanol; 1-(1-methylethyl)-3-propyl-4-[[2'-(1H-tetrazol-5-yl) [1,1'-biphenyl ]-4-yl]methyl]-1H-pyrazole-5-methanol;

3-butyl-1-(1-methylethyl)-4-[[2'-(1H-tetrazol-5-yl) [1,1'-biphenyl ]-4-yl]methyl]-1H-pyrazole-5-carboxaldehyde;

3-butyl-1-(2-methylpropyl)-4-[[2'-(1H-tetrazol-5-yl) [1,1'-biphenyl ]-4-yl]methyl]-1H-pyrazole-5-carboxaldehyde;

3-butyl-1-(2-cyclopropylmethyl)-4-[[2'-(1H-tetrazol-5-yl ) [1,1'-biphenyl ]-4-yl]methyl]-1H-pyrazole -5 -carboxaldehyde;

3-butyl-1-cyclobutyl-4-[[2'-(1H-tetrazol-5-yl) [1,1'-biphenyl]-4-yl]methyl]-1H-pyrazole-5 -carboxaldehyde;

1,3-dibutyl-4-[[2'-(1H-tetrazol-5-yl) [1,1'-biphenyl]-4-yl ]methyl]-1H-pyrazole-5 -carboxaldehyde;

1-(1-methylethyl)-3-propyl-4-[[2'-(1H-tetrazol-5-yl) [1,1'-biphenyl ]-4-yl]methyl]-1H-pyrazole-5-carboxaldehyde;

3-butyl-1-(1-methylethyl)-4-[[2'-(1H-tetrazol-5-yl) [1,1'-biphenyl]-4-yl]methyl]-1H-pyrazole-5-carboxylic acid;

3-butyl-1-(2-methylpropyl)-4-[[2'-(1H-tetrazol-5-yl) [1,1'-biphenyl]-4-yl]methyl]-1H-pyrazole-5-carboxylic acid;

3-butyl-1-cyclobutyl-4-[[2'-(1H-tetrazol-5-yl) [1,1'-biphenyl]-4-yl]methyl]-1H-pyrazole-5-carboxylic acid;

3-butyl-4-[(2'-carboxy[1,1'-biphenyl]-4-yl) methyl]-1-ethyl-1H-pyrazole-5-carboxylic acid;

3-butyl-1-propyl-4-[[2'-(1H-tetrazol-5-yl) [1,1'-biphenyl]-4-yl ]methyl]-1H-pyrazole-5-methanol;

1-ethyl-3-propyl-4-[[2'-(1H-tetrazol-5-yl) [1,1'-biphenyl]-4-yl ]methyl]-1H-pyrazole-5-carboxaldehyde;

1-ethyl-3-propyl-4-[[2'-(1H-tetrazol-5-yl) [1,1'-biphenyl]-4-yl]methyl]-1H-pyrazole-5-carboxylic acid;

1-(1-methylethyl)-3-propyl-4-[[2'-(1H-tetrazol-5-yl) [1,1'-biphenyl ]-4-yl]methyl]-1H-pyrazole-5-carboxylic acid;

1,3-dibutyl-4-[[2'-(1H-tetrazol-5-yl) [1,1'-biphenyl]-4-yl]methyl]-1H-pyrazole-5-carboxylic acid;

3-butyl-4-[(2'-carboxy [1,1'-biphenyl]-4-yl) methyl]-1-(1-methylethyl) -1H-pyrazole-5-carboxylic acid;

3-butyl-1-ethyl-4-[[2'-(1H-tetrazol-5-yl) [1,1'-biphenyl]-4-yl ]methyl]-1H -pyrazole-5-carboxaldehyde;

3-butyl-1-propyl-4-[[2'-(1H-tetrazol-5-yl) [1,1'-biphenyl]-4-yl ]methyl]-1H-pyrazole-5-carboxaldehyde;

1-(2-methylpropyl)-3-propyl-4-[[2'-(1H-tetrazol-5-yl) [1,1'-biphenyl]-4-yl]methyl]-1H-pyrazole-5-carboxylic acid;

3-butyl-1-propyl-4-[[2'-(1H-tetrazol-5-yl) [1,1'-biphenyl]-4-yl ]methyl]-1H-pyrazole-5-carboxylic acid;

3-butyl-1-ethyl-4-[[2'-(1H-tetrazol-5-yl) [1,1'-biphenyl]-4-yl]methyl]-1H-pyrazole-5-carboxylic acid;

3-butyl-1-(2-cyclopropylmethyl)-4-[[2'-(1H-tetrazol-5-yl) [1,1'-biphenyl ]-4-yl]methyl]-1H-pyrazole-5-carboxylic acid;

3-butyl-1-ethyl-4-[[2'-[[(trifluoromethyl)sulphonyl]amino][1,1'-biphenyl]-4-yl]methyl]-1H-pyrazole-5-carboxylic acid;

1-ethyl-3-propyl-4-[[2'-[[(trifluoromethyl)sulphonyl]amino][1,1'-biphenyl]-4-yl]methyl]-1H-pyrazole-5-carboxylic acid;

5-[4'-[[3-butyl-1-ethyl-5-(methoxymethyl)-1H-pyrazol-4-yl]methyl][1,1'-biphenyl]-2-yl]-1H-tetrazole; and the physiologically acceptable salts, solyates and metabolically labile esters thereof.

In accordance with the first aspect of the present invention, there is also provided a compound of the general formula (I) above or a physiologically acceptable salt, solvate or metabolically labile ester thereof wherein $R^1$ represents a $C_{1-6}$alkyl group;

$R^2$ represents a hydrogen atom or group selected from $C_{1-6}$alkyl, $C_{3-7}$cycloalkyl, $C_{3-7}$cycloalkyl$C_{1-4}$alkyl, fluoro$C_{1-6}$alkyl, phenyl, —$(CH_2)_kCOR^5$ or —$(CH_2)_kSO_2R^5$;

$R^3$ represents a group selected from $C_{1-6}$alkyl substituted by a hydroxy or $C_{1-6}$alkoxy group, —$(CH_2)_mR^6$ or —$(CH_2)_nCOR^7$;

$R^4$ represents a group selected from —$CO_2H$, —$NHSO_2CF_3$ or a C-linked tetrazolyl group;

$R^5$ represents the group $NR^{10}R^{11}$;

$R^6$ represents a benzyloxy group;

$R^7$ represent a hydrogen atom or a hydroxy group;

$R^{10}$ and $R^{11}$ each independently represent a hydrogen atom or a $C_{1-4}$alkyl group;

k represents zero or an integer from 1 to 4;

m represents an integer from 1 to 4; and n represents zero or an integer from 1 to 4.

The physiologically acceptable acid addition salts of the compounds of formula (I) may be derived from inorganic or organic acids. Examples of such salts include hydrochlorides, hydrobromides, sulphates, phosphates, benzoates, methanesulphonates or trifluoroacetates.

The compounds may also form salts with suitable bases. Examples of such salts are alkali metal (e.g. sodium or potassium), alkaline earth metal (e.g. calcium or magnesium), ammonium and substituted ammonium (e.g. dimethylammonium, triethylammonium, 2-hydroxyethyldimethylammonium, piperazinium, N,N-dimethylpiperazinium, tetraalkylammonium, piperidinium, ethylenediammonium and choline).

It will be appreciated that, for pharmaceutical use the salts referred to above will be physiologically acceptable, but other salts may find use, for example, in the preparation of the compounds of formula (I) and the physiologically acceptable salts thereof.

It will be further appreciated that the compounds of general formula (I) may be chemically modified in the form of compounds which in vivo (for example, by enzymic attack) will provide the parent compounds of general formula (I). Such prodrugs may be, for example, physiologically acceptable metabolically labile ester derivatives. These may be formed by esterification, for example of any of the carboxylic acid groups in the parent compound of general formula (I), with prior protection of any other reactive groups present in the molecule. Examples of such esters include lower alkyl esters (e.g. methyl or ethyl esters), alkenyl esters (e.g. vinyl or alkyl esters), alkynyl esters(e.g. ethynyl or propynyl esters), alkoxyalkyl esters, (e.g. methoxymethyl or 2-methoxyethyl esters), alkylthioalkyl esters (e.g. methylthiomethyl esters) haloalkyl esters (e.g. 2-iodoethyl or 2,2,2,-trichloromethyl esters), alkanoyloxyalkyl esters (e.g. acetoxymethyl, 1-acetoxyethyl or pivaloyloxymethyl esters), alkoxycarbonyloxyalkyl esters (e.g. 1-ethoxycarbonyloxyethyl or 1-methoxycarbonyloxyethyl esters), aroyloxyalkyl esters (e.g. benzoyloxymethyl or 1-benzoyloxyethyl esters), substituted or unsubstituted aralkyl esters (e.g. benzyl or 4-amidobenzyl esters), substituted or unsubstituted aminoethyl esters (e.g aminoalkyl or 2—N,N-dimethylaminoethyl esters) or hydroxyalkyl esters (e.g. 2-hydroxyethyl or 2,3-dihydroxypropyl esters).

In addition to the above ester derivatives the present invention includes within its scope compounds of general formula (I) in the form of other physiologically acceptable equivalents, i.e. physiologically acceptable compounds which, like the metabolically labile esters, are converted in vivo into the parent compounds of general formula (I).

According to a second aspect of the invention we provide a compound of general formula (I) or a physiologically acceptable salt, solvate or metabolically labile ester thereof for use in therapy.

In particular, the compounds of the invention may be used in the treatment or prophylaxis of hypertension. They are also potentially useful for the treatment of cognitive disorders such as dementia (e.g. Alzheimer's disease) and other diseases such as renal failure, hyperaldosteronism, cardiac insufficiency, congestive heart failure, post-myocardial infarction, cerebrovascular disorders, glaucoma and disorders of intracellular homeostasis.

According to a further aspect of the invention we provide a compound of general formula (I) or a physiologically acceptable salt, solvate or metabolically labile ester thereof for use in the treatment of the aforementioned diseases, especially hypertension.

According to another aspect of the invention we provide a compound of general formula (I) or a physiologically acceptable salt, solvate or metabolically labile ester thereof for the manufacture of a therapeutic agent for the treatment of the aforementioned diseases, especially hypertension.

According to a further aspect of the invention we provide a method of treating the aforementioned diseases, especially hypertension, which method comprises administering an effective amount to a patient in need of such treatment of a compound of general formula (I) or a physiologically acceptable salt, solvate or metabolically labile ester thereof.

It will be appreciated that the compounds of general formula (I) or a physiologically acceptable salt, solvate or metabolically labile ester thereof may advantageously be used in conjunction with one or more other therapeutic agents, such as for example diuretics and/or different antihypertensive agents such as B-blockers, calcium channel blockers or ACE inhibitors. It is to be understood that such combination therapy constitutes a further aspect of the present invention.

It will be further appreciated that reference herein to treatment extends to prophylaxis as well as to the treatment and relief of established symptoms.

While it is possible that a compound of general formula (I) may be administered as the raw chemical it is preferable to present the active ingredient as a pharmaceutical formulation.

The compounds of general formula (I) and their physiologically acceptable salts, solvates and metabolically labile esters may be formulated for administration in any convenient way, and the invention also includes within its scope pharmaceutical compositions comprising at least one compound of general formula (I) or a physiologically acceptable salt, solvate or metabolically labile ester thereof adapted for use in human or veterinary medicine. Such compositions may be presented for use in conventional manner in admixture with one or more physiologically acceptable carriers or excipients. The carrier(s) must be 'acceptable' in the sense of being compatible with the other ingredients of the formulation and not deleterious to the recipient thereof.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

It will be appreciated that both tablets and capsules may be manufactured in the form of sustained release formulations, such that they provide a controlled continuous release of the compounds according to the invention over a period of hours.

The compounds of general formula (I) and their physiologically acceptable salts, solvates and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insulator.

The pharmaceutical formulations according to the invention may also contain other active ingredients such as antimicrobial agents, or preservatives.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, when the compositions comprise dosage units, each unit will preferably contain 0.1 mg to 500 mg, advantageously where the compounds are to be administered orally 1 mg to 400 mg of the active compound. The daily dosage as employed for adult human treatment will preferably range from 0.1 mg to 2 g, most preferably from 1 mg to 1 g which may be administered in 1 to 4 daily doses.

The compounds of the invention may be prepared by a number of processes as described below wherein the various groups are as defined for general formula (i) unless otherwise specified.

It will be appreciated by a person skilled in the art that where necessary, reactive or labile groups in the following processes may be protected in a conventional manner using, for example, one of the groups described in process (C) hereinafter.

Thus, according to a further aspect of the present invention we provide a process (A) for preparing the compounds of general formula (I) which comprises treating a compound of general formula (II)

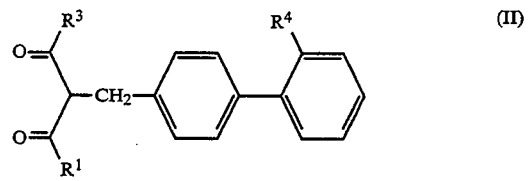

(wherein $R^1$, $R^3$ and $R^4$ are as defined in general formula (I)) with a hydrazine of formula (III)

$R^2NHNH_2$         (III)

(wherein $R^2$ is as defined in general formula (I)) followed by the removal of any protecting groups where present, as described hereinafter.

The reaction is preferably effected in a solvent such as an aqueous alcohol e.g. ethanol, an ether e.g tetrahydrofuran or dioxan, a substituted amide e.g dimethylformamide, acetonitrile or water at a temperature in the range of 0° C. to reflux and preferably at room temperature.

The intermediate diketones of formula (II) are novel compounds and form a further aspect of the invention.

In another general process (B) a compound of general formula (I) may be obtained by interconversion of another compound of general formula (I). Thus for example, when $R^2$ represents a hydrogen atom, such a compound may be converted into a compound of general formula (I) wherein $R^2$ represents a group —($CH_2$)$_k$$COR^5$ or —($CH_2$)$_k$$SO_2R^5$ by reaction with L—($CH_2$)$_k$$COR^5$ or L—($CH_2$)$_k$$SO_2R^5$, respectively (wherein L represents a leaving group, for example, a halogen atom such as a chlorine, bromine or iodine, or a hydrocarbylsulphonyloxy group such as methanesulphonyloxy, or p-toluenesulphonyloxy). The reaction is conveniently effected in a suitable solvent such as a substituted amide e.g dimethylformamide or an ether e.g tetrahydrofuran in the presence of a base such as sodium hydride or sodium amide, at a temperature in the range 0° C. to reflux, and preferably at room temperature.

In an alternative example of process (B) a compound of general formula (I) wherein $R^2$ is a hydrogen atom may be converted into a compound of general formula (I) wherein $R^2$ represents a $C_{1-6}$alkyl,$C_{3-7}$cycloaklyl or $C_{3-7}$cycloalkylC$_{1-4}$alkyl group, or a group —($CH_2$)$_k$$COR^5$ or —($CH_2$)$_k$$SO_2R^5$ where k is 1 to 4, by reaction with a corresponding alkylating agent, for example, an alkylhalide such as an alkyliodide. The reaction is conveniently effected in a suitable solvent such as a substituted amide e.g. dimethylformamide or an ether e.g. tetrahydrofuran in the presence of a base such as potassium carbonate or sodium hydride, at a temperature in the range of 0° C. to reflux, and preferably at room temperature.

It will also be appreciated that other substituents in a compound of general formula (I) may be modified by techniques well known in the art to produce alternative compounds of general formula In another general process (C) a compound of general formula (I) may be obtained by deprotection of a protected intermediate of general formula (Ia)

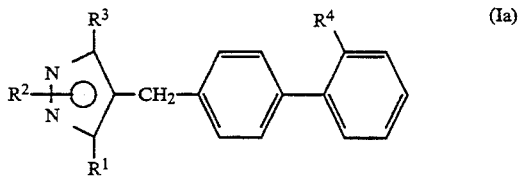

(wherein $R^1$, $R^2$, $R^3$ and $R^4$ are as defined in general formula (I) except that at least one reactive group is blocked by a protecting group). The protecting groups may be any conventional protecting groups, for example as described in "Protective Groups in Organic Synthesis" by Theodora Greene (John Wiley and Sons Inc., 1981). Examples of carboxyl protecting groups include $C_{1-6}$alkyl such as methyl or t-butyl, or $C_{7-10}$aralkyl such as benzyl.

When $R^4$ is a tetrazolyl group, this may be protected with, for example, the trityl group —C(phenyl)$_3$, or a p-nitrobenzyl or 1-ethoxyethyl group.

Deprotection to yield the compound of general formula (I) may be effected using conventional techniques. Thus, for example, aralkyl groups may be cleaved by hydrogenolysis in a suitable organic solvent such as an alcohol, e.g. ethanol, in the presence of a noble metal catalyst such as palladium or an oxide thereof on a support such as charcoal, and conveniently at room temperature and pressure. Carboxyl protecting groups such as alkyl groups may be cleaved by hydrolysis using a base such as an alkali metal hydroxide (e.g. sodium hydroxide or potassium hydroxide) in a suitable solvent (e.g. an aqueous alcohol such as methanol or ethanol) at any suitable temperature up to reflux. Deprotection of the tetrazolyl group when protected with a trityl group may be effected by acid hydrolysis using trifluoroacetic acid, a sulphonic acid such as dl-10-camphor sulphonic acid, or a mineral acid such as hydrochloric acid in a suitable solvent such as methanol, ethanol, tetrahydrofuran or mixtures thereof conveniently at room temperature to reflux. Alternatively, when possible, deprotection of the tetrazolyl group can be effected by catalytic hydrogenation as previously described.

In another general process (D) a compound of general formula (I) in which the substituent $R^4$ represents a C-linked tetrazolyl group, may also be prepared from a compound of general formula (IV)

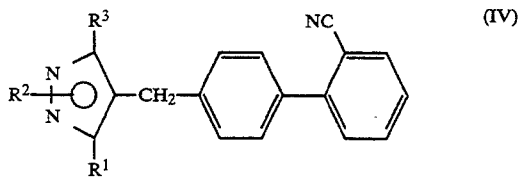

(wherein, $R^1$, $R^2$ and $R^3$ are as defined in general formula (I)) by reaction with a suitable azide such as sodium azide, ammonium azide (preferably prepared in situ from sodium azide and ammonium chloride), trialkyl-(e.g. triethyl)ammonium azide (preferably prepared in situ from sodium azide and a trialkylamine (e.g. triethylamine)), a trialkylsilylazide (e.g. trimethylsilylazide) or an alkyl azide e.g. tributyl tin azide. The reaction is conveniently effected in a solvent such as xylene, an ether, for example, dimethoxyethane or tetrahydrofuran, or a substituted amide, for example, dimethylformamide, at an elevated temperature, such as the reflux temperature of the solvent, for between 1 and 10 days. Where the azide is tributyl tin azide the reaction may conveniently be effected in the absence of a solvent at a temperature between room temperature and 180° C. Such a reaction leaves the tetrazolyl group protected with a tributyl tin group, which can readily be removed using aqueous base or acid. Where aqueous base is used to effect this deprotection, the compound may be treated with an aqueous acid to liberate the tetrazole.

Compounds of general formula (IV) may be prepared by processes analogous to those described herein commencing from a compound of formula (XV).

The Intermediate compounds of general formula (Iv) are novel compounds and form a further aspect of the present invention.

In another general process (E) a compound of general formula (I) in which the substituent $R^4$ represents —NHSO$_2$CF$_3$, may be prepared from a compound of general formula (V)

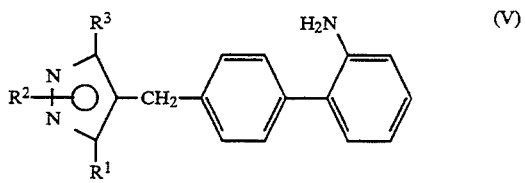

(wherein $R^1$, $R^2$ and $R^3$ are as defined in general formula (I)) by reaction with trifluoromethanesulphonic anhydride or trifluoromethylsulphonyl chloride, in a suitable solvent such as a halogenated hydrocarbon, e.g. dichloromethane or chlorform.

Compounds of general formula (V) may be prepared by processes analogous to those described herein commencing from a compound of formula (XVI) or a nitro precursor thereof.

Alternatively, compounds of general formula (V) may be prepared by a Curtius rearrangement of a compound of formula (I) wherein $R^4$ is —CO$_2$H (provided that this is the only carboxyl group in the molecule) using, for example, diphenylphosphorylazide in the presence of a base such as triethylamine and in a solvent such as an alcohol (e.g. tert-butanol) to form a carbamate followed by deprotection of the amine in a conventional manner, for example by acid hydrolysis using hydrochloric acid in a solvent such as ethanol.

The intermediate compounds of general formula (V) and their acid addition salts are novel compounds and form a further aspect of the present invention.

In another general process (F) a compound of general formula (I) may be prepared by treating a compound of formula (VI) with a compound of formula (VII)

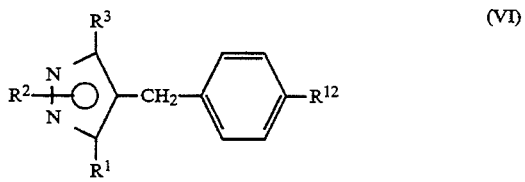

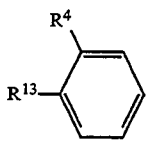

(where one of $R^{12}$ and $R^{13}$ represents a halogen atom, for example, bromine or iodine, and the other represents the group —B(OH)$_2$ or an ester thereof, and $R^1$, $R^2$, $R^3$ and $R^4$ are as defined in general formula (I)).

The reaction may be effected in the presence of a transition metal catalyst such as tetrakis(triphenylphosphine)palladium (0), in a suitable solvent such as an ether (e.g. 1,2-dimethoxyethane or tetrahydrofuran) or an aromatic hydrocarbon (e.g. benzene). The reaction is preferably carried out in the presence of a base such as an alkali or alkaline earth metal carbonate (e.g. sodiumcarbonate) at a suitable temperature up to reflux.

The intermediate compounds of formula (VI) are novel compounds and form a further aspect of the present invention.

In another general process (G) a compound of general formula (I) wherein $R^3$ represents the group —(CH$_2$)$_n$COR$^7$ where n is zero and $R^7$ is C$_{1-6}$alkoxy, may be prepared by reacting a biphenyl compound of formula (VIII)

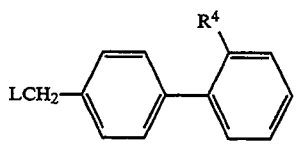

(wherein $R^4$ is as defined in general formula (I) and L is a leaving group as defined above) with a compound of formula (IX)

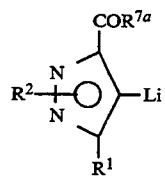

(wherein $R^1$ and $R^2$ are as defined in general formula (i) and $R^{7a}$ is a C$_{1-6}$alkoxy group).

The reaction is conveniently effected at a temperature between −100° C. and room temperature in a suitable solvent such as an ether, for example, tetrahydrofuran, dimethoxyethane or diethyl ether.

In the processes (A), (B), (C), (D), (E), (F) and (G) described above, the compounds of general formula (I) may be obtained in the form of a salt, conveniently in the form of a physiologically acceptable salt. Where desired, such salts may be converted into the corresponding free acids or free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

The intermediate compounds of general formula (II) may be prepared from a compound of formula (X)

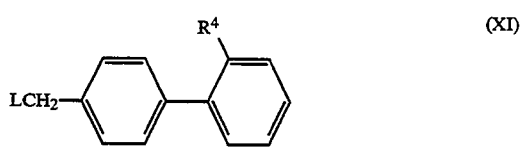

(wherein $R^1$ and $R^3$ are as defined in general formula (I)) by condensation with a compound of formula (XI)

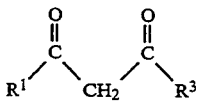

(wherein $R^4$ is defined in general formula (I) and L is a leaving group, for example a halogen atom such as chlorine, bromine or iodine, or a hydrocarbylsulphonyloxy group such as methanesulphonyloxy, or p-toluenesulphonyloxy). The reaction is preferably effected under basic conditions, for example, in the presence of sodium hydride, potassium carbonate or sodium methoxide. The reaction is conveniently effected in a solvent such as acetonitrile or an ether e.g. tetrahydrofuran or dioxan, a ketone e.g. butanone or acetone, or a substituted amide e.g. dimethylformamide, at a temperature between 0° C. and the reflux temperature of the solvent.

Compounds of formula (X) may be prepared by reaction of a compound of formula (XII)

$R^1COCH_3$ (XII)

With a compound of formula (XIII)

$R^3CO_2CH_3$ (XIII)

preferably in the presence of a base such as sodium amide, sodium hydride or tetra-n-butyl ammonium fluoride. The reaction is conveniently effected in a solvent such as an ether e.g. tetrahydrofuran or dioxan, or a halogenated hydrocarbon e.g. dichloromethane at a temperature between 0° C. and the reflux temperature of the solvent.

Compounds of formula (VIII) and (XI) may be prepared from a compound of formula (XIV)

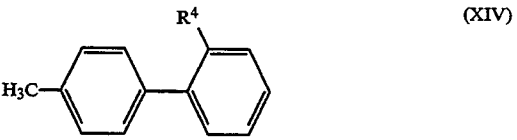

using any suitable reagent well known in the art for converting the methyl group in formula (XIV) into the group —CH$_2$L (wherein L is as defined above). Thus for example, when L is a halogen atom, a compound of formula (XIV) can be converted into a compound of formula (XI) using N-chloro amides, tert-butyl hypochlorite or N-bromosuccinimide. Halogenation may be catalysed by light, thus the reaction mixture can be illuminated with a suitable artificial light source, and preferably in the presence of a free radical initiator such as azobisisobutyronitrile (AIBN) or dibenzoyl peroxide. The reaction may be conveniently effected in a solvent such as a halogenated hydrocarbon, e.g. carbon tetrachloride at an elevated temperature such as the reflux temperature of the solvent.

Compounds of formula (XIV) in which R⁴ represents a C-linked tetrazolyl group may be prepared from a compound of formula (XV)

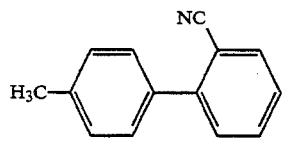
(XV)

using the reagents and conditions described in process (D).

Compounds of formula (XIV) in which R⁴ represents the group —NHSO₂CH₃ may be prepared from a compound of formula (XVI)

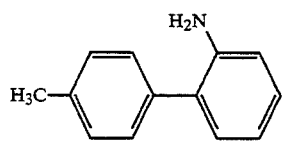
(XVI)

using the reagents and conditions described in process (E).

Compounds of formula (XIV) in which R⁴ represents —COOH or —NHSO₂CF₃, and compounds of formulae (XV) and (XVI), may be prepared by reaction of a compound of formula (XVII)

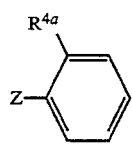
(XVII)

(wherein Z represents a bromine or iodine atom or the group —OSO₂CF₃, and R⁴ª represents either —COOH, —NHSO₂CF₃, a nitrile or amino group or a group convertible thereto by standard methodology) with a corresponding 4-methylbenzeneboronic acid derivative in the presence of a palladium (0) compound such as tetrakis(triphenylphosphine) palladium (0) in a solvent such as dimethoxyethane in the presence of a base such as sodium carbonate or thallium hydroxide. The reaction is conveniently effected at an elevated temperature, such as the reflux temperature of the solvent.

Compounds of formulae (VI) or (VII) where R¹² or R¹³ represents —B(OH)₂ may be prepared from the corresponding halides by lithiation at low temperature followed by reaction with a suitable boronic acid ester (e.g. triisopropylborate) and subsequent hydrolysis with water or an acid (e.g. hydrochloric acid).

Alternatively, compounds of formula (VI) wherein R¹² represents Hal may be prepared by the reaction of a compound of formula (XVIII)

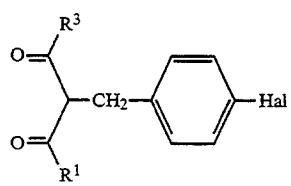
(XVIII)

with a compound of formula (III) under the reaction conditions of general process (A).

Compounds of formula (XVIII) may be prepared by reaction of a compound of formula (XIX)

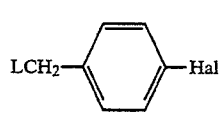
(XIX)

(wherein Hal is a bromine or iodine atom and L is a leaving group) with a compound of formula (X) under basic conditions, for example, in the presence of sodium hydride, potassium carbonate or sodium methoxide. The reaction is conveniently effected in a solvent such as acetonitrile or an ether e.g. tetrahydrofuran, a ketone, e.g. acetone or a substituted amine e.g. dimethylformamide, at a temperature between 0° C. and the reflux temperature of the solvent.

Compounds of formula (IX) may be prepared by lithiation of a compound of formula (XX)

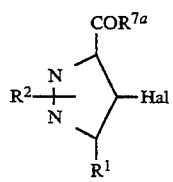
(XX)

The reaction may be effected using an alkyllithium compound, for example, tert-butyl lithium at a temperature between −100° C. and room temperature, in a suitable solvent such as an ether, for example, tetrahydrofuran, dimethoxyethane or diethyl ether.

Compounds of formula (XX) may be prepared by halogenation of a compound of formula (XXI)

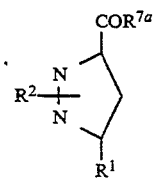
(XXI)

using standard methodology described herein above.

Compounds of formula (XXI) may be prepared by the reaction of a compound of formula (X) wherein R³ represents —(CH₂)ₙCOR⁷ (where n is zero and R⁷ is C₁₋₆alkoxy) with a compound of formula (III) using the method of general process (A).

Intermediates of formulae (III), (VII), (VIII), (XII), (XIII), (XVI) and (XVII) are either known compounds or may be prepared by methods analogous to those described herein or used for the preparation of the known compounds.

The following examples illustrate the invention. Temperatures are in 0° C. "Dried" refers to drying using magnesium sulphate. Thin layer chromatography was carried out on silica, using one of the following solvent systems: A—ether:hexane, B—dichloromethane:ethanol:ammonia, C—ether:petroleum ether (40°-60°), D—ethyl acetate:hexane, E—ethyl acetate:ethanol, F—ether:acetic acid, G—ether:hexane:acetic acid, or H—ethyl acetate: acetic acid. The following abbreviations are used: DFC—dry flash chromatography on silica gel (Merck 9385); THF—tetrahydrofuran; DME—dimethoxyethane; AIBN—azobisisobutyronitrile; DMF—N,N-dimethylformamide; TFA—trifluoroacetic acid.

INTERMEDIATE 1

1-Methoxy-2,4-octandione

2-Hexanone (96.8 g) was added dropwise over 15 min under nitrogen to a stirred suspension of sodium amide (37.7 g) in dry ether (1 liter) at room temperature. The mixture was stirred for 12 min, a solution of methyl methoxyacetate (50.3 g) in dry ether (150 ml) was added dropwise over 20 min, and the mixture was heated under reflux for 2 h. The mixture was cooled, poured into ice and 2N hydrochloric acid (600 ml) and the aqueous layer extracted with ether (4×300 ml). The organic layers were washed with 8% sodium bicarbonate solution and brine, dried and evaporated to give an orange liquid (102 g). Purification by DFC, eluting with System A (5:95) gave a yellow liquid (36 g).

T.l.c. (System A 5:95) Rf 0.1.

INTERMEDIATE 2

1,1-Dimethylethyl 4'-bromomethylbiphenyl-3-carboxylate (a) 1,1-Dimethylethyl 2-bromobenzoate A solution of o-bromobenzoic acid (1 g), N, N'-dicyclohexyl carbodiimide (1.129 g), t-butanol (405 mg) and 4-dimethylaminopyridine (61 mg) in dry ether (20 ml) was stirred at room temperature for 18 h. The resulting precipitate was filtered off and the filtrate evaporated to give a colourless solid which was triturated under petroleum ether (40°-600°) (20 ml) and filtered. The filtrate was evaporated to give a pale yellow oil (0,994 g). b.p. 80°-84°/0.35 mmHg.

(b) 1,1-Dimethylethyl 4'-methylbiphenyl-2-carboxylate

A mixture of Intermediate 2a (2.0 g) 4-methylbenzeneboronic acid (1.17 g), tetrakis(triphenylphosphine) palladium (0) (269 mg) and sodium carbonate solution (1M; 21 ml) in DME (80 ml) was heated under reflux for 18 h. The solvent was evaporated and the residue partitioned between ether (3×50 ml) and sodium carbonate (2N; 100 ml) and the combined organic extracts were washed with brine (2×100 ml) and dried. The solvent was evaporated to give a pale-yellow oil which was purified by short-path column chromatography on silica gel (Merck 7729; 40 g). Elution with System C (1:40) gave a colourless, mobile oil (1.88 g).

T.l.c (System C 1:40) Rf 0.3.

(c) 1,1-Dimethylethyl 4'-bromomethylbiphenyl-2-carboxylate

A mixture of Intermediate 2b (1.825 g), [-bromosuccinimide (1.21 g) and dibenzoyl peroxide (130 mg) in carbon tetrachloride (30 ml) was heated under reflux for 18 h. The solvent was evaporated in vacuo and the residue partitioned between ether (3×50 ml) and sodium bisulphite solution (50 ml). The combined organic extracts were dried and the solvent evaporated to give a yellow oil which was purified by short-path column chromatography on silica gel (Merck 7729; 60 g). Elution with System C (1:50) gave a colourless crystalline solid (1.15 g).

T.l.c (System C 1:50) Rf 0.25.

INTERMEDIATE 3

2-(4-Bromomethyl(phenyl))-2'-(triphenylmethyl)tetrazol-1-yl benzene (a) 2-(4-Methylphenyl)benzonitrile To a solution of o-bromobenzonitrile (40 g) and 4-methylbenzeneboronic acid (33 g) in DME (2 liters) was added tetrakis (triphenylphosphine) palladium (0) (7.58 g) and then sodium carbonate (1M, 592 ml). The mixture was stirred vigorously and heated at reflux for 18 hours. The solvent was removed in vacuo and the dark residue partitioned between ether (800 ml) and sodium carbonate (1M, 800 ml); the aqueous phase was extracted with ether (3×400 ml). The combined organic phases were dried and concentrated in vacuo to afford an orange oil which was crystallised from System C (1:3) using activated charcoal as a decolourising agent to afford a white solid (33.0 g).

T.l.c. System A (1:9) Rf 0.30

(b) 2-(4-Methylphenyl)-1H-tetrazol-1-yl benzene

A mixture of Intermediate 3a (7 g) and tributyl tin azide (24 g) was heated at 160° C. Further amounts of Intermediate 3a were added after 2h (4 g) and a further 1.5h (2 g) and heating then continued for another 1.5h. The cooled reaction mixture diluted with ether (200 ml) and extracted with aqueous sodium hydroxide solution (2M;50 ml). The aqueous mixture was poured into cold concentrated HCl (50 ml) and the white solid filtered and air-dried. This solid was crystallised from toluene (200 ml) to give the title compound as cream microcrystals (10.2 g).

T.l.c. ether Rf. 040

(c) 2-(4-Methylphenyl)-2'-(triphenylmethyl)tetrazol-1-yl benzene

To a suspension of Intermediate 3b (12.2 g) in dry dichloromethane (100 ml) was added triethylamine (12.8 ml). Trityl chloride (14.6 g) was added followed by N,N-dimethylaminopyridine (251 mg) and the resultant solution was stirred at room temperature for 16 h. The reaction mixture was partitioned between water (200 ml) and dichloromethane (200 ml). The separated organic phase was washed with water (200 ml), dried and concentrated in vacuo to give the title compound as a cream-coloured solid (21.2 g).

T:l.c. System A (1:1) Rf 0.55

(d) 2-(4-Bromomethyl(phenyl))-2'-(triphenylmethyl) tetrazol-1-yl benzene

To a solution of Intermediate 3c (21.1 g) in carbon tetrachloride (600 ml) was added N-bromosuccinimide (8.3 g), and the mixture heated almost to reflux. Dibenzoyl peroxide (854 mg) was added and the mixture heated at reflux for 3.5 h. Further dibenzoyl peroxide (800 mg) was added and the reaction mixture heated at reflux for a further 60 h. Further N-bromosuccinimide (4.2 g) and dibenzoyl peroxide (854 mg) were added and the mixture heated at reflux in the presence of a 200W lamp for 3 h. The cooled mixture was filtered and the filtrate washed with water (2×150 ml), dried and concentrated in vacuo to afford the title compound as a cream glassy solid (23 g).

T.l.c (ethyl acetate:petroleum ether 1:1) Rf 0.90.

INTERMEDIATE 4

1,1-Dimethylethyl 4'-[2-(methoxyacetyl)-3-oxoheptanyl][1,1'-biphenyl]-2-carboxylate Intermediate 1 (13.4 g) was heated under reflux with Intermediate 2 (30.0 g) and anhydrous potassium carbonate (10.8 g) in acetone (390 ml) with stirring under nitrogen for 6 h. The solvent was evaporated and the residue partitioned between water (300 ml) and ether (3×200 ml); the organic extracts were washed with brine, dried and evaporated to give an orange oil (39.5 g). Purification by DFC eluting with System A (1:4) gave the title compound as a pale yellow oil (25 g).
T.l.c. System A (1:3) Rf 0.1.

INTERMEDIATE 5

1-Methoxy-3-[[2'-[2-(triphenylmethyl)-2H-tetrazol-5-yl][1,1'-biphenyl]-4-yl)methyl]-2f4-octandione Sodium hydride (80% dispersion in oil, 200 mg) was added to a stirred solution of Intermediate 1 (0.96 g) in dry THF (20 ml) at room temperature under nitrogen, and stirring was continued at room temperature for 40 min. A solution of Intermediate 3 (2.08 g) in THF (5 ml) was added, and the mixture was heated under reflux for 22 h. The mixture was poured into water (50 ml) and extracted with ether (3×40 ml); the organic layers were washed with brine, dried and evaporated to give a dark yellow oil (2.38 g). Purification by DFC eluting with System A (20:80 to 50:50) gave the title compound as pale yellow oil (0.8 g).
T.l.c. (System A 40:60) Rf 0.2.

INTERMEDIATE 6

1,1-Dimethylethyl 4'-[[3-butyl-5-(methoxymethyl)-1H-pyrazol-4-yl]methyl][1,1'-biphenyl]-2-carboxylate Intermediate 4 (0.5 g) was stirred at room temperature with hydrazine hydrate (85%, 0.086 ml) in absolute ethanol (15 ml) under nitrogen for 16 h. The solvent was evaporated to give a colourless oil (375 mg). Purification by DFC eluting with System B (98:2:0.2) gave a colourless oil (325 mg).
T.l.c. System C (50:50), Rf 0.2.

INTERMEDIATE 7

(a) 1,1-Dimethylethyl 4'-[[5-butyl-3-(methoxymethyl)-1-phenyl-1H-pyrazol-4-yl]methyl][1,1'-biphenyl]-2-carboxylate; and (b) 1,1-Dimethylethyl 4'-[[3-butyl-5-(methoxymethyl)-1-phenyl-1H-pyrazol-4-yl]methyl][1,1'-biphenyl]-2-carboxylate Intermediate 4 (1.0 g) was stirred with phenylhydrazine (0.224 ml) in ethanol (absolute, 20 ml) at room temperature under nitrogen for 16 h and heated under reflux for 24 h. The solvent was evaporated to give an orange oil (1.22 g). Purification by DFC eluting with System A (10:90-30:70) gave:

(a) intermediate 7a as a pale yellow oil (229 mg), T.l.c. (System C 50:50) Rf 0.4, and (b) Intermediate 7b as a pale yellow oil (256 mg), T.l.c. (System C 50:50) Rf 0.75.

INTERMEDIATE 8

(a) 1,1-Dimethylethyl 4'-[[3-butyl-5-(methoxymethyl)-1-(2,2,2-trifluoroethyl) -1H-pyrazol-4-yl]methyl][1,1'-biphenyl]-2-carboxylate; and (b) 1,1-Dimethylethyl 4'-[[5.-butyl-3-(methoxymethyl)-1-(2,2,2-trifluoroethyl) -1H-pyrazol-4-yl]methyl][1,1'-biphenyl]-2-carboxylate Intermediate 4 (0.5 g) was stirred at room temperature under nitrogen with 2,2,2-trifluoroethylhydrazine (70% in water, 0.204 ml) in ethanol (10 ml) for 24 h. The solvent was evaporated and the residue (0.7 g) purified by DFC eluting with System A (10:90→50:50) to give:

(a) Intermediate 8a as a pale yellow oil (180 mg), T.l.c (System A 50:50) Rf 0.55; and (b) Intermediate 8b as a colourless oil (239 mg), T.l.c. (System A 50:50) Rf 0.25.

INTERMEDIATE 9

5-[4'-[[3-Butyl-5-(methoxymethyl)-1H-pyrazol-4-yl)]methyl][1,1'-biphenyl]-2-yl]-2-(triphenylmethyl)-2H-tetrazole Intermediate 5 (150 mg) was stirred at room temperature under nitrogen with hydrazine hydrate (80% hydrazine hydrate; 0.018 ml) in absolute ethanol (3 ml) for 3 days. The solvent was evaporated and the residue purified by DFC, eluting with ether to give the title compound as a colourless gum (78 mg).
T.l.c. (ether) Rf 0.2.

INTERMEDIATE 10

(a) 5-[4'-[[3-Butyl-5-(methoxymethyl)-1-(2,2,2-trifluoroethyl)-1H-pyrazol -4-yl]methyl][1,1'-biphenyl]-2-yl]-2-(triphenylmethyl)-2H-tetrazole; and (b) 5-[4'-[[5-Butyl-3-(methoxymethyl)-1-(2,2,2-trifluoroethyl)-1H-pyrazol -4-yl]methyl][1,1'-biphenyl]-2-yl]-2-(triphenylmethyl)-2H-tetrazole Intermediate 5 (0.805 g) was stirred at room temperature with 2,2,2trifluoroethylhydrazine (70% solution in water, 0.304 ml) in ethanol for 21 h. The solvent was evaporated and the residue purified by DFC eluting with System A (10:90 to 60:40) to give:

g(a) intermediate 10a, T.l.c (System A 50:50) Rf 0.35; and (b) Intermediate 10b, T.l.c. (System A 50:50) Rf 0.2.

INTERMEDIATE 11

(a) 1,1'-Dimethylethyl 4'-[[1-(2-amino-2-oxoethyl)-5-butyl-3-(methoxymethyl) -1H-pyrazol-4-yl]methyl][1,1'-biphenyl]-2-carboxylate; and (b) 1,1'-Dimethylethyl 4'-[[1-(2-amino-2-oxoethyl)-3-butyl-5-(methoxymethyl) -1H-pyrazol-4-yl]methyl][1,1'-biphenyl]-2-carboxylate Sodium hydride (52 mg) was added to a stirred solution of Intermediate 6 (0.5 g) in dry DMF (5 ml), and stirring was continued at room temperature under nitrogen for 1.5 h. Chloroacetamide (122 mg) was added and stirring was continued at room temperature for 3 h. The mixture was partitioned between water (30 ml) and ethyl acetate (3×20 ml); the organic extracts were washed with 50:50 brine:water (3×30 ml), dried and evaporated to give a pale yellow gum (658 mg). Purification by DFC, eluting with System D (50:50) followed by ethyl acetate, and System E (95:5) gave:

(a) Intermediate 11a as a colourless oil (291 mg), T.l.c. (ethyl acetate) Rf 0.15; and (b) Intermediate 11b as a pale yellow gum (277 mg), T.l.c (ethyl acetate) Rf 0.3.

INTERMEDIATE 12

(a) 1,1'-Dimethylethyl 4'-[[5-butyl-3-(methoxymethyl)-1-methyl-1H-pyrazol -4-yl]methyl][1,1'-biphenyl]-2-carboxylate; and (b) 1,1'-Dimethylethyl 4'-[[3-butyl-5-(methoxymethyl)-1-methyl-1H-pyrazol -4-yl]methyl][1,1'-biphenyl A mixture of Intermediate 6 (1.0 g), methyl iodide (330 mg) and potassium carbonate (320 mg) in DMF (30 ml) was stirred at room temperature for 3 days. The reaction mixture was poured into water and extracted with ethyl acetate. The combined organic extracts were washed with water, brine, dried and evaporated to give a colourless oil. This was chromatographed on silica gel eluting with System A (20:80→80:20) followed by ether to give:

(a) Intermediate 12a as a colourless oil (124 mg), T.l.c (System F 99:1) Rf 0.3; and (b) Intermediate 12b as a colourless oil (330 mg), T.l.c (System A 50:50) Rf 0.50.

INTERMEDIATE 13

(a) 1,1-Dimethylethyl 4'-[[5-butyl-1-[(dimethylamino)sulphonyl]-3-(methoxymethyl) -1H-pyrazol-4-yl]methyl]-[1,1'-biphenyl]-2carboxylate; and (b) 1,1-Dimethylethyl 4'-[[3-butyl-1-[(dimethylamino)sulphonyl]-5-(methoxymethyl) -1H-pyrazol-4-yl]methyl][1,1'-biphenyl]-2-carboxylate Sodium hydride (52 mg; 80% dispersion in oil) was added to a stirred solution of Intermediate 6 (0.5 g) in dry DMF (5 ml) at room temperature under nitrogen. After stirring for 0.5 h, N,N-dimethylsutphamoyl chloride (0.185 ml) was added at 0° and stirring was continued at 0° for 2 h. The mixture was partitioned between water (30 ml) and ethyl acetate (3×20 ml); the organic layers were washed with 50:50 brine:water (3×30 ml) and brine (30 ml), dried and evaporated to give a pale yellow oil (0.76 g). Purification by DFC eluting with System A (20:80 to 40:60) gave:

(a) Intermediate 13a as a colourless oil (296 mg), T.l.c. (System A 50:50) Rf 0.3; and (b) Intermediate 13b as a colourless oil (23ling), T.l.c. (System A 50:50) Rf 0.45.

INTERMEDIATE 14

(a) 5-[4'-[[3-Butyl-1-ethyl-5-(methoxymethyl)-1H-pyrazol-4-yl]methy][1,1'-biphenyl]-2-yl]-2-(triphenylmethyl)-2H-tetrazole; and (b) 5-[4'-[[5-Butyl-1-ethyl-3-(methoxymethyl)-1H-pyrazol-4-yl]methy][1,1'-biphenyl]-2-yl]-2-(triphenylmethyl)-2H-tetrazole A solution of Intermediate 9 (1.26 g) in dry DMF (5 ml) was added dropwise to a suspension of sodium hydride (60% in oil, 116 mg) in dry DMF (5 ml). The resulting pale yellow solution was stirred at room temperature for 0.5h, then a solution of the ethyl iodide (0.16 ml) in dry DMF (1 ml) was added dropwise. The mixture was stirred at room temperature for 2h, then partitioned between water (20 ml) and ethyl acetate (3×20 ml). The combined organic extracts were washed with brine/water 1:1 (3×50 ml) and dried. The solvent was evaporated to give a pale yellow foam (1.283 g) which was purified by short-path column chromatography on silica gel (Merck 7729) eluting with System C (1:142:1) to give:

(a) Intermediate 14a as a pale yellow gum (569 mg) n.m.r. (CDCl$_3$, 250 MHz) δ 0.85 (3H,t), 1.2–1.6 (4H, m), 1.40 (3H, t), 2.45 (2H, t), 3.20 (3H, s), 3.70 (2H, s), 4.12 (2H, q), 4.20 (2H, s), 6.90–7.50 (7H, m), 7.85–7.9 (1H); and (b) Intermediate 14b (654 mg) n.m.r. (CDCl$_3$, 250 MHz) δ 0.85 (3H, t), 1.2–1.35 (4H, m), 1.41 (3H, t), 2.40 (2H, t), 3.30 (3H, s), 3.72 (2H, s) 4.05 (2H, q), 4.28 (2H, s), 6.90–7.50 (7H, m), 7.85–7.9 (1H).

INTERMEDIATE 15

(a) 5-[4'-[[3-Butyl-1-[(dimethylamino)sulphonyl)-5-(methoxymethyl) -1H-pyrazol-4-yl ]methyl][1,1'-biphenyl]-2-yl]-2-(triphenylmethyl) -2H-tetrazole; and (b) 5-[4'-[[5-Butyl-1-[(dimethylamino)sulphonyl]-3-(methoxymethyl) -1H-pyrazol-4-yl]methyl][1,1'-biphenyl]-2-yl]-2-triphenylmethyl) -2 H-tetrazole Sodium hydride (60% in oil; 93 mg) was added portionwise to a solution of Intermediate 9 (1.0 g) in dry DMF (10 ml) at room temperature under nitrogen. The resulting pale yellow suspension was stirred at room temperature for 0.5 h, cooled to 0° C. then a solution of dimethylsulphamoyl chloride (222 mg) in dry DMF (0.5 ml) was added dropwise. The resulting mixture was stirred at room temperature for 2 h, then partitioned between ethyl acetate (3×20 ml) and water (20 ml). The combined organic extracts were washed with brine/water (1:1) (3×20 ml) and dried. The solvent was evaporated to give a pale yellow foam (1.27 g), which was purified by short-path column chromatography on silica gel (Merck 7729) eluting with System A (1:2) to give:

(a) Intermediate 15a as a colourless foam (462 mg) T.l.c. (System C 1:1) Rf 0.4; and (b) Intermediate 15b as a colourless foam (615 mg) T.l.c (System C 1:1) Rf 0.35.

INTERMEDIATE 16

Phenylmethoxy-2,4-octandione

2-Hexanone (26.7 g) was added dropwise over 5 min at room temperature to a stirred suspension of sodium amide (10.4 g) in dry ether (290 ml) under nitrogen. The reaction mixture was stirred for 13 min. and a solution of methyl phenylmethoxyacetate (24.0 g) in dry ether (40 ml) was added dropwise over 12 min. The mixture was then heated at reflux for 3 h, cooled, and then poured into ice (400 g) and 2N HCl (200 ml). The aqueous phase was extracted with ether (2×350 ml) and the combined etheral solution washed with 8% sodium bicarbonate solution (2×250 ml), water (200 ml) and brine (200 ml), then dried and evaporated to leave a yellow liquid (35.8 g). This was purified by column chromatography on silica gel eluting with System A (2:98) to give the title compound as a yellow oil (10.95 g).

T.l.c. (System C 1:9) Rf. 0.50

INTERMEDIATE 17

1-[(Phenylmethoxy)methyl]-3-[[2'-[2-(triphenylmethyl)-2H-tetrazol-5-yl][1,1'-biphenyl]-4-yl ) methyl]-2,4-octandione To a suspension of sodium hydride (60% in oil; 820 mg) in THF (63 ml) at 0° C. was added a solution of Intermediate 16 (4 g) in THF (6.5 ml) dropwise over 35 min. The reaction mixture was stirred at room temperature for 40 min prior to the addition of Intermediate 3 (6.38 g) in THF (21 ml) over 15 min. The resultant reaction mixture was heated at reflux for 17 h. The reaction mixture was concentrated in vacuo and the residue partitioned between water (80 ml) and ether (3×80 ml). The combined organic layers were dried and concentrated in vacuo and then purified by column chromatography on silica gel eluting with System C (1:8) to afford the title compound (3.0 g) as a white solid.

T.l.c (System C 1: 3 ) Rf 0.28

INTERMEDIATE 18

5-[4'-[[3-Butyl-5-[(phenylmethoxy)methyl]-1H-pyrazol-4-yl]methyl][1,1'- biphenyl]-2-yl]-2-(triphenylmethyl )-2H-tetrazole Hydrazine hydrate (85%; 0.85 ml) was added to a solution of Intermediate 17 (10.17 g) in ethanol (100 ml) containing dichloromethane (20 ml). The mixture was stirred at room temperature for 2 days. The solvent was evaporated in vacuo and the residue purified by column chromatography on silica gel eluting with System C (4:1) and increasing the polarity to neat ether, to give the title compound as a colourless foam (7.67 g).

T.l.c (ether) Rf 0.5.

INTERMEDIATE 19

Phenylmethoxy-2,4-heptandione

From 2-heptanone and methyl phenylmethoxyacetate according to the method of Intermediate 16.

T.l.c. System A (1:10) Rf 0.39

INTERMEDIATE 20

1-[(Phenylmethoxy)methyl]-3-[[2'-[2-(triphenylmethyl)-2H-tetrazol-5-yl][1,1'-biphenyl]-4-yl]methyl]-2,4-heptandione From Intermediate 19 according to the method of Intermediate 17.

T.l.c. System A (1:4) Rf 0.20

INTERMEDIATE 21

5-[4'-[[3-Propyl-5-[(phenylmethoxy)methyl]-1H-pyrazol-4-yl]methyl][1,1'-biphenyl]-2-yl]-2-(triphenylmethyl)-2H-tetrazole From Intermediate 20 according to the method of Intermediate 18.

T.l.c. System A (5:1) Rf 0.25

INTERMEDIATE 22

(a) 5-[4'-[[3-Butyl-1-ethyl-5-[(phenylmethoxy)methyl]-1H-pyrazol-4-yl]methyl][1,1'-biphenyl]-2-yl]-2-(triphenylmethyl)-2H-tetrazole; and (b) 5-[4'-[[5-Butyl-1-ethyl-3-[(phenylmethoxy)methyl]-1H-pyrazol-4-yl]methyl][1,1'-biphenyl]-2-yl]-2-(triphenylmethyl)-2H-tetrazole A solution of Intermediate 18 (3.0 g) in dry DMF (15 ml) was added dropwise to a suspension of sodium hydride (60% dispersion in oil; 254 mg), in dry DMF (15 ml) at 0° under nitrogen. The mixture was stirred at 5°–10° for 15 mins, then a solution of ethyl iodide (660 mg) in dry DMF (1 ml) was added dropwise. The mixture was allowed to warm to room temperature over 1 h. The mixture was partitioned between water (50 ml) and ethyl acetate (3×25 ml) and the combined organic extracts washed with brine/water 1:1 (2×50 ml) and dried. The solvent was evaporated to give a pale yellow gum (3.19 g) which was purified by column chromatography on silica gel eluting with System A (1:241:1) to give the title compound:

(a) Example 22a as a colourless foam (1.33 g), T.l.c System A (1:2) Rf 0.2; and (b) Example 22b as a colourless foam (1.60 g), T.l.c. System A (1:2) Rf 0.5.

Similarly prepared from Intermediate 18 and the appropriate alkyl halide were:

INTERMEDIATES 23a AND b (a) 5-[4'-[[3-Butyl-1-(1-methylethyl)-5-[(phenylmethoxy)methyl]-1H-pyrazol -4-yl]methyl][1,1'-biphenyl]-2-yl]-2-(triphenylmethyl)-2H-tetrazole T.l.c. System A (1: 2 ) Rf 0.45

(b) 5-[4'-[[5-Butyl-1-(1-methylethyl)-3-[(phenylmethoxy)methyl]-1H-pyrazol -4-yl]methyl][1,1'-biphenyl]7.2-yl]-2-(triphenylmethyl)-2H-tetrazole T.l.c. System A (1:2) Rf 0.35

INTERMEDIATES 24a AND b (a) 5-[4'-[[3-Butyl-1-(2-methylpropyl)-5-[(phenylmethoxy)methyl]-1H-pyrazol -4-yl]methyl][1,1'-biphenyl]-2-yl]-2-(triphenylmethyl)-2H-tetrazole T.l.c. System A (2:3) Rf 0.3

(b) 5-[4'-[[5-Butyl-1-(2-methylpropyl)-3-[(phenylmethoxy)methyl]-1H-pyrazol -4-yl]methyl][1,1'-biphenyl]-2-yl]-2-(triphenylmethyl)-2H-tetrazole T.l.c. System A (1:2) Rf 0.25

INTERMEDIATES 25a AND b (a) 5-[4'-[[3-Butyl-1-(2-cyclopropylmethyl)-5-[(phenylmethoxy) methyl]-1H-pyrazol-4-yl]methyl][1,1'-biphenyl]-2-yl]-2-(triphenylmethyl) -2 H-tetrazole T.l.c. System A (2:3) Rf 0.45

(b) 5-[4'-[[5-Butyl-1-(2-cyclopropylmethyl)-3-[(phenylmethoxy) methyl]-1H-pyrazol-4-yl)methyl][1,1'-biphenyl]-2-yl)-2-(triphenylmethyl) -2H -tetrazole T.l.c. System A (2:3) Rf 0.42

INTERMEDIATES 26a AND b (a) 5-[4'-[[3-Butyl-1-cyclobutyl-5-[(phenylmethoxy)-methyl],1H-pyrazol -4-yl]methyl][1,1'-biphenyl]-2-yl]-2-(triphenylmethyl)-2H-tetrazole T.l.c. System A (1:1) Rf 0.71

(b) 5-[4'-[[5-Butyl-1-cyclobutyl-3-[(phenylmethoxy)methyl]-1H-pyrazol -4-yl]methyl][1,1'-biphenyl]-2-yl]-2-(triphenylmethyl)-2H-tetrazole T.l.c. System A (1:1) Rf 0.68

INTERMEDIATES 27a AND b (a) 5-[4'-[[3-Butyl-1-methyl-5-[(phenylmethoxy)methyl]1H-pyrazol-4-yl]methyl][1,1'-biphenyl]-2-yl]-2-(triphenylmethyl)-2H-tetrazole T.l.c. System A (4:1) Rf 0.44

(b) 5-[4'-[[5-Butyl-1-methyl-3-[(phenylmethoxy)methyl]-1H-pyrazol-4-yl]methyl][1,1'-biphenyl]-2-yl]-2-(triphenylmethyl)-2H-tetrazole T.l.c. System A (4:1) Rf 0.34

INTERMEDIATES 28a AND b (a) 5-[4'-[[3-Butyl-1-propyl-5-[(phenylmethoxy)methyl]-1H-pyrazol-4-yl]methyl][1,1'-biphenyl]-2-yl]-2-(triphenylmethyl)-2H-tetrazole T.l.c. System A (2:1) Rf 0.60˙

(b) 5-[4'-[[5-Butyl-1-propyl-3-[(phenylmethoxy)methyl]-1H-pyrazol-4-yl]methyl][1,1'-biphenyl )-2-yl]-2-(triphenylmethyl)-2H-tetrazole T.l.c. System A (2:1) Rf 0.44

INTERMEDIATES 29a AND b (a) 5-[4'-[[1,3-Dibutyl-5-[(phenylmethoxy)methyl]-1H-pyrazol-4-yl]methyl][1,1'-biphenyl]-2-yl]-2-(triphenylmethyl)-2H-tetrazole T.l.c. System G (60:30:1) Rf 0.80

(b) 5-[4'-[[1,5-Dibutyl-3-[(phenylmethoxy)methyl]-1H-pyrazol-4-yl]methyl][1,1'-biphenyl]-2-yl]-2-(triphenylmethyl)-2H-tetrazole T.l.c. System G (60:30:1) Rf 0.66

Similarly prepared from Intermediate 21 and the appropriate alkyl halide were:

INTERMEDIATES 30a AND b (a) 5-[4'-[[Ethyl-3-propyl-5-[(phenylmethoxy)methyl]-1H-pyrazol-4-yl]methyl][1,1'-biphenyl]-2-yl]-2-(triphenylmethyl)-2H-tetrazole T.l.c. System A (3:1) Rf 0.75

(b) 5-[4'-[[1-Ethyl-5-propyl-3-[(phenylmethoxy)methyl],1H-pyrazol-4-yl]methyl][1,1'-biphenyl]-2-yl]-2-(triphenylmethyl)-2H-tetrazole T.l.c. System A (3:1) Rf 0.60

INTERMEDIATES 31a AND b (a) 5-[4'-[[1-(1-Methylethyl)-3-propyl-5-[(phenylmethoxy)methyl]-1H-pyrazol -4-yl]methyl][1,1'-biphenyl]-2-yl]-2-(triphenylmethyl)-2H-tetrazole T.l.c. System A (1:1) Rf 0.50

(b) 5-[4'-[[1-(1-Methylethyl)-5-propyl-3-[(phenylmethoxyl)methyl]-1H-pyrazol -4-yl]methyl][1,1'-biphenyl]-2-yl]-2-(triphenylmethyl)-2H -tetrazole T.l.c. System A (1:1) Rf 0.36

INTERMEDIATE 32

Phenylmethoxy-2,4-hexandione

2-Butanone (47.65 ml) was added dropwise over 10 min to a mechanically stirred suspension of sodium amide (95%; 20.78 g) dry ether (600 ml) at room temperature under nitrogen. The reaction mixture was stirred at room temperature for 15 min. A solution of methyl phenylmethoxyacetate (48.0 g) in dry ether (50 ml) was added dropwise over 13 min at room temperature under nitrogen, and the reaction progressed according to the method of Intermediate 16, to give the title compound as a yellow oil (23.35 g)

T.l.c. System A (1:10) Rf 0.15.

INTERMEDIATE 33

1-[(phenylmethoxy)methyl]-3- [[2-[2-(triphenylmethyl)-2H-tetrazol-5-yl][1,1'-biphenyl]-4-yl]methyl]-2,4-hexandione From Intermediate 32 according to the method of Intermediate 20.

T.l.c. System A (1:4) Rf 0.30.

INTERMEDIATE 34

5-[4'-[[3-Ethyl-5-[(phenylmethoxy)methyl]-1H-pyrazol-4-yl]methyl][1,1'-biphenyl]-2-yl]-2-(triphenylmethyl)-2H-tetrazole From Intermediate 33 according to the method of Intermediate 21.

T.l.c. System A (6:1) Rf 0.21.

INTERMEDIATES 35a AND b (a) 5-[4'-[[1,3-Diethyl-5-[(phenylmethoxy)methyl]-1H-pyrazol-4-yl]methyl][1,1'-biphenyl]-2-yl]-2-(triphenylmethyl)-2H-tetrazole; and (b) 5-[4'-[[1,5-Diethyl-3-[(phenylmethoxy)methyl]-1H-pyrazol-4-yl]methyl][1,1'-biphenyl]-2-yl]-2-(triphenylmethyl)-2H-tetrazole From Intermediate 34 according to the method of Intermediate 22 gave:

(a) Intermediate 35a as a yellow gum (1.1ag) T.l.c. System A (3:1) Rf 0.60

(b) Intermediate 35b as a yellow gum (1.40 g) T.l.c. System A (3:1) Rf. 0.40.

INTERMEDIATE 36

1,1-Dimethylethyl 4'-[3-oxo-2-(phenoxyacetyl)heptanyl][1,1'-biphenyl]-2-carboxylate From Intermediate 16 and Intermediate 2 according to the method of Intermediate 17.

T.l.c. System A (1:5) Rf 0.25.

INTERMEDIATE 37

1,1-Dimethylethyl 4'-[[3-butyl-5-[(phenylmethoxy)methyl]-1H-pyrazol-4-yl]methyl][1,1'-biphenyl]-2-carboxylate From Intermediate 36 according to the method of Intermediate 18.

T.l.c. System A (3:2) Rf 0.15.

INTERMEDIATE 38a AND b (a) 1,1-Dimethylethyl 4'-[[3-butyl-1-ethyl-5-[(phenylmethoxy) methyl]-1H-pyrazol-4-yl]methyl][1,1'-biphenyl]-2-carboxylate; and (b) 1,1-Dimethylethyl 4'-[[5-butyl-1-ethyl-5-[(phenylmethoxy) methyl]-1H-pyrazol-4-yl]methyl][1,1'-biphenyl]-2-carboxylate From Intermediate 37 and ethyl iodide according to the method of Intermediate 22.

Intermediate 38a: T.l.c. System A (1:1) Rf 0.35
Intermediate 38b: T.l.c. System A (1:1) Rf 0.2.

INTERMEDIATE 39a AND b (a) 1,1-Dimethylethyl 4'-[[3-butyl-1-(1-methylethyl)-5-[(phenylmethoxy)methyl]-1H-pyrazol-4-yl]methyl][1,1'-biphenyl]-2-carboxylate; and (b) 1,1-Dimethylethyl 4'-[[5-butyl-1-(1-methylethyl)-3-[(phenylmethoxy)methyl]-1H-pyrazol-4-yl]methyl][1,1'-biphenyl]-2-carboxylate From Intermediate 37 and isopropyl iodide according to the method of Intermediate 22.

Intermediate 39a: T.l.c. System A (1:2) Rf 0.3
Intermediate 39b: T.l.c. System A (1:2) Rf 0.2.

INTERMEDIATE 40

1,1-Dimethylethyl 4'-[[3-butyl-1-ethyl-5-[(hydroxymethyl)-1H-pyrazol-4-yl]methyl][1,1'-biphenyl]-2-carboxylate From Intermediate 38a according to the method of Example 26.

T.l.c. ethyl acetate:hexane (1:1) Rf. 0.4.

INTERMEDIATE 41

1,1-Dimethylethyl 4'-[[3-butyl-5-(hydroxymethyl)-1-(1-methylethyl)-1H-pyrazol-4-yl]methyl][1,1'-biphenyl]-2-carboxylate From Intermediate 39a according to the method of Example 26.

T.l.c. System A (1:1) Rf. 0.25.

INTERMEDIATE 42

1,1-Dimethylethyl 4'-[[3-butyl-1-ethyl-5-formyl-1H-pyrazol-4-yl]methyl][1,1'-biphenyl]-2-carboxylate From Intermediate 40 according to the method of Example 42.

T.l.c. System A (1: 1 ) Rf 0.7.

INTERMEDIATE 43

1,1-Dimethylethyl 4'-[[3-butyl-5-formyl-1-(1-methylethyl)-1H-pyrazol-4-yl]methyl][1,1'-biphenyl]-2-carboxylate From Intermediate 41 according to the method of Example 42.

T.l.c. System A (1:1) Rf. 0.7.

INTERMEDIATE 44

3-Butyl-4-[[2'-[(1,1-dimethylethoxy)carbonyl][1,1'-biphenyl]-4yl-]methyl]-1-ethyl-1H-pyrazole-5-carboxylic acid From Intermediate 42 according to the method of Example 50.

T.l.c. ether:hexane:acetic acid (50:50:1) Rf. 0.6

INTERMEDIATES 45a AND b (a) 5-[4'-[[1-(2-Methylpropyl)-3-propyl-5-[(phenylmethoxy)methyl]-1H -pyrazol-4-yl]methyl][1,1'-biphenyl]-2-yl]-2-(triphenylmethyl)-2H-tetrazole; and (b) 5-[4'-[[1-(2-Methylpropyl)-5-propyl-3-[(phenylmethoxy)methyl]-1H -pyrazol-4-yl]methyl][1,1'-biphenyl]-2-yl]-2-(triphenylmethyl)-2H-tetrazole From Intermediate 21 and 2-methylpropyl iodide according to the method of Intermediate 22.

Intermediate 45a: T.l.c. System A (1:1) Rf 0.27
Intermediate 45b: T.l.c. System A (1:1) Rf 0.19

INTERMEDIATE 46

3-Butyl-4-[[2'-(1,1-dimethylethoxy)carbonyl][1,1'-biphenyl]-4-yl ]methyl]-1-(1-methylethyl )-1H-pyrazole-5-carboxylic acid From Intermediate 43 according to the method of Example 50.

T.l.c. System G (20:20:1) Rf 0.65

EXAMPLE 1

4'-[[3-Butyl-5-(methoxymethyl)-1H-pyrazol-4-yl]methyl][1,1'-bimpenyl]-2-carboxylic acid trifluoroacetate (1:1) salt A solution of Intermediate 6 (320 mg) in dry dichloromethane (30 ml) was treated with TFA (1 ml) and the reaction stirred at room temperature for 5 h. The volatiles were removed in vacuo and the residue triturated with ether to give the title compound (162 mg) as a white solid.

T.l.c. (System C 50:50), Rf 0.05.

Assay Found: C, 60.7; H,5.7; N, 5.5.

$C_{23}H_{26}N_2O_3 \cdot CF_3CO_2H$ requires C, 61.0; H,5.5; N,5.7%.

EXAMPLE 2

4'-[[5-Butyl-3-(methoxymethyl)-1-phenyl-1H-pyrazol-4-yl]methyl][1,1, -biphenyl]-2-carboxylic acid A solution of Intermediate 7a in TFA (3 ml) was stirred at 200 for 90 min. The reaction mixture was concentrated in vacuo and the residue was dissolved in dichloromethane (15 ml). The organic layer was extracted with sodium bicarbonate solution (8%; 3×30 ml). The combined extracts were acidified to pH=1 with dilute hydrochloric acid and then extracted with dichloromethane (3×30 ml). The combined extracts were washed with brine (30 ml), dried and concentrated in vacuo to yield a the title compound as a pale brown solid (157 mg). m.p. 85°–91° C.

T.l.c. (System B 50:8:1) Rf 0.44.

EXAMPLE 3

4'-[[3-Butyl-5-(methoxymethyl)-1-phenyl-1H-pyrazol-4yl]methyl][1,1'-biphenyl]-2-carboxylic acid Intermediate 7b (256 mg) was stirred at room temperature with TFA (1 ml) in dry dichloromethane (5 ml) overnight. The solvent was evaporated to give a brown oil (280 mg). Purification by DFC eluting with System G gave the title compound as a pale yellow gum (95 mg).

T.l.c. (System G 50:50:1) Rf 0.4

Analysis Found: C,76.6; H,6.9; N, 5.7.

$C_{29}H_{30}N_2O_3$ requires C,76.6; H,6.65 N, 6.2%

EXAMPLE 4

4'-[[3-Butyl-5-(methoxymethyl)-1-(2,2,2-trifluoroethyl )-1H-pyrazol -4-yl]methyl][1,1'-biphenyl]-2-carboxylic acid Intermediate 8a (180 mg) was dissolved in 98% formic acid (4 ml) and the solution allowed to stand at room temperature overnight (16 h). The excess formic acid was evaporated and the residue azeotroped with toluene (20 ml) to give a colourless gum (175 mg). Purification by DFC eluting with System G (50:50:1) gave the title compound as a colourless gum (90mg). T.l.c (System G 50:50:1) Rf 0.5.

Analysis Found: C,65.5; H,5.9; N, 6.1.

$C_{25}H_{27}F_3N_2O_3$ requires C, 65.2; H,5.9; N, 6.1%.

EXAMPLE 5

4'-[[5-Butyl-3-(methoxymethyl)-1-(2,2,2.-trifluoroethyl)-1H-pyrazol -4-yl]methyl) [1,1'-biphenyl]-2-carboxylic acid Intermediate 8b was treated according to the method of Example 4 to give the title compound as a colourless gum (89 mg).

T.l.c (System F 99:1) Rf 0.75.

Analysis Found: C,65.5; H,6.2; N,5.9.

$C_{25}H_{27}F_3N_2O_3$ requires C,65.2; H,5.9; N, 6.1%.

EXAMPLE 6

5-[4'-[[3-Butyl-5-(methoxymethyl)-1H-pyrazol-4-yl]methyl][1,1'-biphenyl]-2-yl]-1H-tetrazole Intermediate 9 (40 mg) was treated with 2N hydrochloric acid (1 ml) in THF (5 ml) at room temperature and the mixture was stirred at room temperature for 7 h. The mixture was partitioned between ethyl acetate (15 ml) and dilute aqueous sodium hydroxide (2 ml of 2N in 15 ml of water). The aqueous layer was neutralized with excess saturated aqueous ammonium chloride (10 ml) and extracted with ethyl acetate (3×10 ml). The latter organic layers were washed with brine, dried and evaporated to give the title compound as a colourless gum (12 mg). T.l.c. (System H 99:1) Rf 0.3. n.m.r. (CDCl$_3$,250 MHz) δ 0.85 (3H, t), 1.15–1.55 (4H, m), 2.45 (2H, t), 3.2 (3H, s), 3.77 (2H, s), 4.14 (2H, s), 7.0–8.0 (8H, m), 8.8 (2H, broad s).

EXAMPLE 7

5-[4'-[[3-Butyl-5-(methoxymethyl)-1-(2,2,2-trifluoroethyl)-1H-pyrazol-4-yl]methyl][1,1'-biphenyl],2-yl]-1H-tetrazole dl-10—Camphor sulphonic acid (20 mg) was added to a stirred solution of Intermediate 10a (103 mg) in THE (10 ml) and methanol (3 ml), and stirring was continued at room temperature for 16 h. The solvent was evaporated to give a pale yellow oil, which was purified by DFC eluting with System G to give the title compound as a white solid (39 mg). m.p. 45°–51° C. T.l.c. (System F 99:1) Rf 0.5.

EXAMPLE 8

5-[4-[[5-Butyl-3-(methoxymethyl)-1-(2,2,2-trifluoroethyl)-1H-pyrazol-4-yl]methyl][1,1'-biphenyl]-2-yl]-1H-tetrazole dl-10—Camphor sulphonic acid (40 mg) was added to a stirred solution of Intermediate 10b (203 mg) in THF (20ml) and methanol (6 ml), and stirring was continued at room temperature for 20 h. The solvent was evaporated to give a pale yellow oil. Purification by DFC eluting with System G (50:50:1 to 100:0:1) gave a colourless oil (129 mg) which was dissolved in chloroform (10 ml). n-Heptane was added, and the solvents evaporated to give the title compound as a white foam (101 mg) m.p. 48°–500.

T.l.c. (System F 99:1) Rf 0.4.

EXAMPLE 9

4'-[[1-(2-Amino-2-oxoethyl)-5-butyl-3-(methoxymethyl)-1H-pyrazol-4-yl]methyl][1,1'-biphenyl]-2-carboxylic acid Intermediate 11a was treated according to the method of Example 4 to give the title compound as a white solid (170 mg) m.p 204°–206°.

T.l.c. (System H 98:2) Rf 0.15

EXAMPLE 10

4'-[[1-(2-Amino-2-oxoethyl)-3-butyl-5-(methoxymethyl)-1H-pyrazol-4-yl]methyl][1,1'-biphenyl]-2-carboxylic acid Intermediate 11b was treated according to the method of Example 4 to give the title compound as a white solid (126 mg), m.p. 179–1800

T.l.c (System H 98:2) Rf 0.3.

EXAMPLE 11

4'-[[5-Butyl-3-(methoxymethyl)-1-methyl-1H-pyrazol-4-yl]methyl][1,1'-biphenyl]-2-carboxylic acid A solution of Intermediate 12a (114 mg) in dry DMF (5 ml) was treated with TFA (1 ml) at room temperature, and stirring was continued at room temperature for 19 h. The solvent was evaporated to give a pale yellow oil, which was azeotroped with n-heptane to give a yellow oil. Purification by DFC eluting System F (98:2) gave a pale orange oil (110 mg), which was azeotroped with n-heptane to give the title compound as a light brown foam (78 mg) m.p. 45°–51°.

T.l.c. (System F 99:1) Rf 0.2.

EXAMPLE 12

4'-[[3-Butyl-5-(methoxymethyl)-1-methyl-1H-pyrazol-4-yl]methyl][1,1'-biphenyl]-2-carboxylic acid, trifluoroacetate (1: 1) salt Trifluoroacetic acid (1 ml) was added to a stirred solution of Intermediate 12b (310 mg) in dry DMF (10 ml) at room temperature, and stirring was continued at room temperature for 27 h. The solvent was evaporated to give a pale yellow oil (470 mg). n-Heptane (20 ml) was added and evaporated; this was repeated twice to give the title compound as a pale yellow oil (263 mg). T.I.c (Ether) Rf 0.25.

Assay Found: C, 61.9; H, 6.0; N, 5.6.

$C_{24}H_{28}N_2O_3.CF_3COOH$ requires C, 61.65; H, 5.8; N, 5.5%.

EXAMPLE 13

4'-[[5-Butyl-1-[(dimethylamino)sulphonyl]-3-(methoxymethyl)-1H-pyrazol-4-yl]methyl][1,1'-biphenyl]-2,carboxylic acid Intermediate 13a (221 mg) was dissolved in 98% formic acid (4 ml) and the solution allowed to stand at room temperature for 6 h. The excess formic acid was evaporated and the residue azeotroped twice with toluene (2×15 ml) to give a colourless gum (250 mg). Purification by DFC eluting with System A (50:50) and System G (50:50:1) gave the title compound as a colourless gum (169 mg).

T.l.c. (System F 99:1) Rf 0.7

Analysis Found: C,61.5; H,6.4; N,8.7.

$C_{25}H_{31}N_3O_5S$ requires C,61.8; H,6.4; N,8.65%.

EXAMPLE 14

4'-[[3-Butyl-1-[(dimethylamino) sulphonyl]-5-(methoxymethyl)-1H-pyrazol-4-yl]methyl][1,1'-biphenyl]-2-carboxylic acid Intermediate 13b was treated according to the method of example 13 to give the title compound as a white foam (111 mg).

T.l.c. (System F 99:1) Rf 0.8.

Analysis Found: C, 62.0; H, 6.5; N, 8.4.

$C_{25}H_{31}N_3O_5S$ requires C,61.8; H,6.4; N,8.65%.

EXAMPLE 15

5-[4'-[[3-Butyl-1-ethyl-5-(methoxymethyl)-1H-pyrazol-4yl]methyl][1,1'-biphenyl]-2-yl]-1H-tetrazole Concentrated HCl (0.4 ml) was added dropwise to a solution of Intermediate 14a (0.542 g) in methanol (10 ml) containing THF (2 ml). The mixture was stirred at room temperature under nitrogen for 1 h, then basified to pH 10 with sodium hydroxide solution (2N; 3 ml). The solvent was concentrated in vacuo and the residue diluted with water (20 ml). The mixture was extracted with ether (3×20 ml), then the aqueous phase acidified to pH 1 with HCl (2N; 4 ml). The resulting opaque solution was extracted with ethyl acetate (3×30 ml) and the combined ethyl acetate fractions washed with brine (1 ×30 ml) and dried. The solvent was evaporated in vacuo to give a colourless foam (0.34 g) which was purified by column chromatography on silica gel eluting with ethyl acetate/petroleum ether (40°–60°) (2:1) to give the title compound as a colourless foam (304 mg) n.m.r. (MeOD, 250 MHz) δ 0.85 (3H, t), 1.2–1.5 (6H, m), 2.45 (2H, t), 3.25 (3H, s), 3.80 (2H, s), 4.13 (2H, q), 4.38 (2H, s), 7.04 (4H, dd), 7.5–7.68 (4H, m).

T.l.c. (ether/petroleum ether/acetic acid 50:20:0.2) Rf 0.2.

Similarly prepared:

EXAMPLE 16

5-[4'-[[5-Butyl-1-ethyl-3-(methoxymethyl)-1H-pyrazol-4yl]methyl][1,1'-biphenyl]-2-yl-1H-tetrazole as a colourless foam (373 mg).

n.m.r. (MeOD, 250 MHz) 6 0.85 (3H, t), 1.3–1.4 (6H, m), 2.55 (2H, t), 3.25 (3H, s), 3.80 (2H, s), 4.05 (2H, q), 4.28 (2H, s), 7.05 (4H, q), 7.5–7.68 (4H, m).

T.l.c (ether/petroleum ether/acetic acid 50:20:0.2) Rf 0.15.

From the dropwise addition of concentrated HCl (0.4 ml) to a solution of Intermediate 14b (634 mg) in methanol (10 ml) and THF (2 ml).

EXAMPLE 17

5-[4'-[1,3-Butyl-1-[dimethylamino)sulphonoyl]-5-(methoxymethyl)-1H-pyrazol-4-yl]methyl][1,1'-biphenyl]-2-yl]-1H-tetrazole as a colourless foam (288 mg).

n.m.r. (d6-DMSO, 250 MHz) 6 0.80 (3H, t), 1.6–1.30 (2H,m), 1.37–1.49 (2H,m), 2.40 (2H, t), 2.90 (6H, s) 3.28 (3H, s), 3.83 (2H, s), 4.60 (2H, s), 7.0–7.1 (4H, dd), 7.46–7.68 (4H, m).

T.l.c (ethyl acetate) Rf 0.7.

From the dropwise addition of concentrated HCl (0.4 ml) to a solution of Intermediate 15a (430 mg) in methanol (10 ml) and THF (2 ml).

EXAMPLE 18

5-[4'-[[5-Butyl-1-[(dimethylamino)sulphonoyl]-3-(methoxymethyl)-1H-pyrazol-4-yl]methyl][1,1'-biphenyl]-2-yl]-1H-tetrazole as a colourless foam (382 mg).

n.m.r. (d6-DMSO, 250 MHz) δ 0.82 (3H, t), 1.17–1.40 (4H,m), 2.76 (2H, t), 2.95 (6H, s), 3.20 (3H, s), 3.80 (2H, s) 4.20 (2H, s) 7.05 (4H, dd), 7.48–7.68 (4H, m).

T.l.c (ethyl acetate ) Rf 0.7.

From the dropwise addition of concentrated HCl (0.5 ml) to a solution of Intermediate 15b (579 mg) in methanol (10 ml) and THF (2 ml).

EXAMPLE 19

(a) 5-[4'-[[3-Butyl-5-[(phenylmethoxy)methyl]-1-(2,2,2-trifluoroethyl) -1H-pyrazol-4-yl]methyl][1,1'-biphenyl]-2-yl]-1H-trifluoroethyl) -1H-pyrazol-4-yl]methyl][1,1'-biphenyl]-2-yl]-1H-tetrazole; and (b) 5-[4'-[[5-Butyl-3-[(phenylmethoxy)methyl]-1-(2,2,2-trifluoroethyl) -1H-pyrazol-4-yl]methyl][1,1'-biphenyl-2-yl]-1H-tetrazole A solution of Intermediate 17 (2.6 g) and 2,2,2-trifluoroethylhydrazine (70% in water, 584 mg) in ethanol (75 ml) and dichloromethane (25 ml) was heated at reflux for 3 h at which point a further quantity of 2,2,2-trifluoroethylhydrazine (300 mg) was added and the resultant solution heated at reflux for 16 h. Concentrated HCl (1 ml) was added to the cooled reaction mixture and the resultant solution stirred at room temperature for 4 h. The reaction mixture was then adjusted to pH 10 (5N NaOH aq) and the solvents removed in vacuo. The residue was partitioned between water (100 mL) and ether (3×100 ml) and the aqueous phase was acidified to pH 5 (2N HCl aq) and extracted into ethyl acetate (3×100 ml). The combined organic extracts were dried, concentrated in vacuo and purified by column chromatography on silica gel eluting with petroleum ether:ether:methanol:acetic acid (66:34:1:1) to afford:

(a) Example 19a as a white solid (930 mg), T.l.c (petroleum ether:ether:methanol:acetic acid 66:34:1:1) Rf. 0.5 n.m.r. (CDCl$_3$, 250MHz) δ 0.85 (3H, t), 1.28 (2H, sex), 1.51 (2H, pent), 2.48 (2H, t) 3.8 (2H, s), 4.46 (4H, 2 x s), 4.68 (2H, q), 7.2–7.6 (12H,m), 8.1 (1H, d); and (b) Example 19b as a white solid (892 mg). T.l.c (petroleum ether:ether:methanol:acetic acid 66:34:1:1) Rf 0.22 n.m.r. (CDCl$_3$, 250MHz) δ 0.9 (3H, t), 1.3–1.5 (4H,m), 2.62 (2H, t), 3.86 (2H, s), 4.40 (2H, s), 4.42 (2H, s), 4.62 (2H, q), 7.0–7.6 (12H,m), 8.12 (1H, dd).

EXAMPLE 20

5-[4'-[[3-Butyl-1-(2,2,2-trifluoroethyl)-1H-pyrazol-4'-yl]methyl][1,1'-biphenyl]-2-yl]-1H-tetrazole-5-methanol A suspension of palladium on charcoal (10%, 32mg) in ethanol (5 ml) was pre-treated with hydrogen and then a solution of the product of Example 19a (170 mg) in ethanol (3 ml) was added and the resultant mixture was stirred vigorously under an atmosphere of hydrogen for 16 h. The catalyst was removed by filtration and the filtrate concentrated in vacuo. This crude product was purified by column chromatography on silica gel eluting with chloroform/methanol (20:1) to afford the title compound (90 mg) as a white solid.

n.m.r. (CDCl$_3$, 400MHz) δ 0.90 (3H, t), 1.25 (2H, sex), 1.52 (2H, pent), 2.52 (2H, t) 3.0–4.0 (2H, br), 3.82 (2H, s), 4.52 (2H, s), 4.76 (2H, dd), 6.9–7.6 (7H,m), 8.18 (1H,d). I.r. (CHCl$_3$) cm$^{-1}$ 3464 (s), 2873 (m), 1717 (w) 1390 (m).

Similarly prepared:

EXAMPLE 21

5-[4'-[[5-Butyl-3-(hydroxymethyl)-1-(2,2,2-trifluoroethyl)-1H-pyrazol-4-yl]methyl]l1 1'-biphenyl]-2-yl]-1H-tetrazole as a white solid (430 g).

T.l.c (petroleum ether:ether:methanol:acetic acid 50:50:3:3) Rf 0.15 From a solution of the product of Example 19b (450 mg) in ethanol (10 ml).

n.m.r. (d$_6$-DMSO, 250MHz) 0.80 (3H,t), 1.20 (4H,m), 2.50 (2H,m), 3.81 (2H, S), 4.31 (2H, s), 5.00 (2H, dd), 7.00 (2H, d), 7.12(2H, d), 7.5–7.7 (4H,m).

EXAMPLE 22

3-Butyl-4-[[2'-(1H-tetrazol-5-yl)[1,1'-biphenyl]-4-yl]methyl]-1-(2,2,2 -trifluoroethyl)-1H-pyrazole-5-carboxaldehyde Tetra-n-propylammonium perruthenate (2 mg) was added to a mixture of the product of Example 20 (26.5 mg), 4-methylmorpholine N-oxide (10mg) and powdered 4A molecular sieves (152 mg) in a mixture of dry dichloromethane (2 ml) and dry acetonitrile (2 ml) at room temperature under nitrogen. The resultant mixture was stirred at room temperature for 10 min, then the solvent evaporated in vacuo. The residue was purified by short-path column chromatography on silica gel eluting with ether/petroleum ether/acetic acid (70:35:1) to give the title compound as a pale purple foam (18 mg)

n.m.r. (CDCl$_3$; 250 MHz) δ0.9 (3H, t), 1.3–1.4 (2H,m), 1.5–1.6 (2H,m), 2.58 (2H, t), 4.15 (2H, s), 5.18 (2H, q), 7.18–7.65 (7H,m), 8.15 (1H, d), 9.85 (1H, s).

T.l.c. (ether/acetic acid 100: 1) Rf. 0.35

Similarly prepared:

EXAMPLE 23

5-Butyl-4-[[2'-(1H-tetrazol-5-yl)[1,1'-biphenyl]-4-yl]methyl]-1-(2,2,2 -trifluoroethyl)-1H-pyrazole-3-carboxaldehyde as a white solid (20.6mg).

T.l.c. (petroleum ether:ether:methanol:acetic acid 25:25:1:1) Rf 0.6.

n.m.r. (CDCl$_3$, 250MHz), 0.76 (3H,t), 1.1–1.3 (4H,m), 2.45(2H,t), 2.90(2H, s), 4.50 (2H, q), 6.8–7.3 (7H,m), 8.0 (1H,d),9.75 (1H, s).

From the addition of tetra-n-propylammonium perruthenoate (4 mg) to a stirred mixture of the product of Example 21 (104 mg), N-methylmorpholine N-oxide (38.9 mg) and freshly powdered 4A molecular seives (1.1 g) in dry dichloromethane (2.5 ml) and dry acetonitrile (2.5 ml).

EXAMPLE 24

3-Butyl-4-[[2'-(1H-tetrazol-5-yl)[! ,1'-biphenyl]-4-yl]methyl]-1-(2,2,2 -trifluoroethyl)-1H-pyrazole-5-carboxylic acid A solution of sodium chlorite (325 mg; 80%) and sodium dihydrogen phosphate (325 mg) in water (3 ml) was added to a solution of the product of Example 22 (168 mg), 2-methyl-2-butene (2.14 ml;2M in THF), tert-butanol (4 ml) in THF (3 ml) at room temperature and the mixture stirred for 15 min under nitrogen. The solvent was evaporated and the residue was partitioned between water (10 ml) and ethyl acetate (3×10 ml). The combined organic extracts were dried and evaporated to give a pale purple foam (242 mg). The crude material was purified by short-path column chromatography on silica gel eluting with ether/petroleum ether/acetic acid (50:50:1) to give the title compound as a colourless foam (91 mg).

T.l.c (ether/petroleum ether/acetic acid 50:50:1) Rf 0.2.

n.m.r. (MeOD; 250 MHz) 6 0.88 (3H, t), 1.1–1.5 (4H,m), 2.49 (2H, t), 4.15 (2H, s), 5.25 (2H, q) 7.05 (4H, dd), 7.50–7.70 (4H,m).

Similarly prepared:

EXAMPLE 25

5-Butyl-4-[[2'-(1H-tetrazol-5-yl) [1,1'-biphenyl]-4-yl]methyl]-1-(2,2,2-trifluoroethyl)-1H-pyrazole-3-carboxylic acid as a white solid (44 mm).

T.l.c. (ether:petroleum ether:ethanol:acetic acid, 25:25:5:1:1) Rf 0.12.

n.m.r. ($d_6$-DMSO, 400MHz) 6 0.81 (3H, t), 1.24 (4H, br),2.62 (2H, t), 4.05 (2H, s), 5.12 (2H,q), 6.98 (4H, dd), 7.3–7.6 (4H, m).

From a solution of sodium chlorite (171 mg; 80%) and sodium dihydrogen phosphate (171 mg) in water (1.5 ml) added to a stirred solution of the product of Example 23 (88.5 mg), 2-methylbut-2-ene (2M in THF, 1.13 ml), tert-butanol (2 ml) and THF (1.6, ml).

EXAMPLE 26

3-Butyl-1-ethyl-4-[[2'-(1H-tetrazol-5-yl)-[3,1'-biphenyl]-47yl]-methyl]-1H-pyrazole -5-methanol A solution of Intermediate 22a (1.31 g) in absolute ethanol (20 ml) was hydrogenolysed over palladium catalyst (0.4 g, 5% on activated charcoal) over a period of 72 h. A further portion of palladium catalyst (5%;0.4 g) and glacial acetic acid (1 ml) was added and the mixture hydrogenolysed for a further 12 h. A further portion of palladium catalyst (5%;0.4 g) was added with concentrated HCl (1 ml) and the mixture hydrogenolysed for a further 12 h. The catalyst was filtered off and the filtrate evaporated in vacuo to give a pale yellow foam which was purified by column chromatography on silica gel eluting with System F (100:1). The combined fractions were evaporated and azeotroped with heptane to give the title compound as a colourless foam (0.54 g).

T.l.c. System F (100:1) Rf 0.2.

n.m.r. 6 (250 MHz; CDCl₃) 0.82 (3H,t), 1.18–1.30 (5H, t +m), 1.45 (2H,m), 2.40(2H,t), 3.78 (2H,s), 3.98 (2H,q), 4.45 (2H,s), 7.0 (2H, ½ A'BB'), 7.1, (2H, ½ A'BB'), 7.4 (1H, br.d), 7.45–7.52 (12H, m), 7.88 (1H,br.d).

Similarly prepared:

EXAMPLE 27

3-Butyl-1-(1-methylethyl)-4-[[2'-(1H-tetrazol-5-yl)[1,1'-biphenyl]-4-yl]methyl]-1H-pyrazole-5-methanol m.p. 107°–118° C.

T.l.c. ether:acetic acid (100:1) Rf 0.5

From Intermediate 23a.

EXAMPLE 28

5-Butyl-1-(1-methylethyl)-4-[[2'-(1H-tetrazol-5-yl)[1,1'-biphenyl]-4-yl]methyl]-1H-pyrazole-3-methanol m.p. 80°–84° C.

T.l.c. dichloromethane:ether:acetic acid (75:25:1) Rf 0.1

From Intermediate 23b.

EXAMPLE 29

3-Butyl-1-(2-methylpropyl)-4-[[2'-(1H-tetrazol-5-yl)[1,1'-biphenyl]-4-yl]methyl]-1H-pyrazole-5-methanol m.p. 86°–89° C.

T.l.c. dichloromethane:methanol (10:1) Rf 0.45

From Intermediate 24a.

EXAMPLE 30

3-Butyl-1-(2-cyclopropylmethyl)-4-[[2'-(1H-tetrazol-5-yl) [1,1'-biphenyl]-4-yl]methyl]-1H-pyrazole-5-methanol m.p. 87°–98° C.

T.l.c. dichloromethane:methanol (10:1) Rf 0.5

From Intermediate 25a.

EXAMPLE 31

5-Butyl-1-ethyl-4-[[2'-(1H-tetrazol-5-yl) [1,1'-biphenyl]-4-yl]methyl]-1H-pyrazole-3-methanol m.p. 103°–109° C.

T.l.c. dichloromethane:methanol (10:1) Rf 0.5

From Intermediate 22b.

EXAMPLE 32

3-Butyl-1-cyclobutyl-4-[[2'-(1H-tetrazol-5-yl)[1,1"biphenyl]-4-yl]methyl]-1H-pyrazole-5-methanol T.l.c. System F (95:5) Rf 0.47 n.m.r (250MHz; CDCl₃) 6 0.65 (3H,t), 0.95–2.70 (12H,m), 3.58 (2H, s), 4.28 (2H, s), 4.71 (1H,pent), 6.80–7.55 (8H,m).

From Intermediate 26a.

EXAMPLE 33

5-Butyl-1-cyclobutyl-4-[[2'-(1H-tetrazol-5-yl)[1,1"biphenyl]-4yl]methyl]-1H-pyrazole-5-methanol m.p. 85°–90° C.

T.l.c. dichloromethane:ether:acetic:acid (70:10:1) Rf 0.16

From Intermediate 26b.

EXAMPLE 34

3-Butyl-1-methyl-4-[[2'-(1H-tetrazol-5-yl) [1,1'-biphenyl]-4yl]methyl]-1H-pyrazole-5-methanol m.p. 125° C.

T.l.c. dichloromethane:methanol:acetic acid (200:15:1) Rf 0.33

From Intermediate 27a.

EXAMPLE 35

5-Butyl-1-methyl-4-[[2'-(1H-tetrazol-5-yl)[1,1'-biphenyl]-4yl]methyl]-1H-pyrazole-3-methanol m.p. 129° C.

T.l.c. dichloromethane:methanol (9:1) Rf 0.60

From Intermediate 27b.

EXAMPLE 36

1,3-Dibutyl-4-[[2'-(1H-tetrazol-5-yl)[1,1'-biphenyl]-4-yl]methyl]-1H -pyrazole-5-methanol m.p. 125° C.

T.l.c. ether:hexane:acetic acid (60:30:1) Rf 0.13

From Intermediate 29a.

EXAMPLE 37

1,5-Dibutyl-4-[[2'-(1H-tetrazol-5-yl)[1,1'-biphenyl]-4-yl]methyl]-1H -pyrazole-3-methanol m.p. 56°–58° C.

T.l.c. System G (60:30:1) Rf 0.17

From Intermediate 29b.

EXAMPLE 38

1-Ethyl-3-propyl-4-[[2'-(1H-tetrazol-5-yl)[1,1'-biphenyl]-4yl]methyl]-1H-pyrazole-5-methanol
m.p. 77°–82° C.
T.l.c. dichloromethane:methanol (10:1) Rf 0.34
From Intermediate 30a.

EXAMPLE 39

1-Ethyl-5-propyl-4-[[2'-(1H-tetrazol-5-yl)[1,1'-biphenyl]-4yl]methyl]-1H-pyrazole-3-methanol
m.p. 69°–73° C.
T.l.c. dichloromethane:methanol (10:1) Rf 0.45
From Intermediate 30b.

EXAMPLE 40

1-(1-Methylethyl)-3-propyl-4-[[2'-(1H-tetrazol-5-yl)[1,1'-biphenyl]-4-yl]methyl]-1H-pyrazole -5-methanol
m.p. 89°–91° C.
T.l.c. dichloromethane:methanol (10:1) Rf 0.55
From Intermediate 31a.

EXAMPLE 41

1-(1-Methylethyl)-5-propyl-4-[[2'-(1H-tetrazol-5-yl)[1,1'-biphenyl]-4-yl]methyl]-1H-pyrazole-3-methanol
m.p. 86°–90° C.
T.l.c. dichloromethane:methanol (10:1) Rf 0.80
From Intermediate 31b.

EXAMPLE 42

3-Butyl-1-ethyl-4-[[2'-(1H-tetrazol-5-yl) [1,1'-biphenyl]-4yl]methyl]-1H-pyrazole-5-carboxaldehyde Tetra-n-propylammonium perruthenate (TPAP, 22 mg) was added to a mixture of the product of Example 26 (531 mg), 4-methyl morpholine-N-oxide (224 mg) and powdered 4A molecular sieves (6.3 g) in a mixture of dry dichloromethane (15 ml) and acetonitrile (15 ml) at room temperature under nitrogen. The mixture was stirred for 1 h at room temperature. Further portions of TPAP (27 mg), and 4-methyl morpholine-N-oxide (224 mg) were added and the mixture stirred at room temperature for 15 mins. The solvent was evaporated and the residue purified by column chromatography on silica gel eluting with dichloromethane/ether/acetic acid (75:25:1) to give the title compound as a pale purple foam (221 mg).

T.l.c. dichloromethane/ether/acetic acid (75:25:1) Rf 0.6 n.m.r (250MHz; CDCl$_3$) δ 0.90 (3H,t), 1.25–1.45 (5H, t+m) 1.55 (2H, m), 2.55 (2H,t), 4.11 (2H,s), 4.49 (2H,q),7.15 (1H,dd), 7.51–7.63 (2H,2xddd), 8.15 (1H,dd), 9.85 (1H,s).

Similarly prepared:

EXAMPLE 43

3-Butyl-1-(1-methylethyl)-4-[[2'-(1H-tetrazol-5-yl)[1,1'-biphenyl]-4-yl methyl]-1H-pyrazole-5-carboxaldehyde T.l.c. dichloromethane:ether:acetic acid (75:25:1) Rf 0.75 n.m.r. (250MHz, CDCl$_3$) δ 0.9 (3H, t), 1.30 (4H,m), 1.50 (6H,d), 2.60 (2H,t), 4.10 (2H, s), 5.30(1H, sept), 7.20 (4H,A'BB'), 7.4 (1H,br.d), 7.50–7.65 (2H,m), 8.25 (1H, br.d), 9.85 (1H, s).

From the product of Example 27.

EXAMPLE 44

5-Butyl-1-(1-methylethyl)-4-[[2'-(1H-tetrazol-5-yl)[1,1'-biphenyl]-4-yl]methyl]-1H-pyrazole-3-carboxaldehyde.
m.p. 146°–148° C.
T.l.c. dichloromethane:ether:acetic acid (75:25:1) Rf 0.5
From the product of Example 28.

EXAMPLE 45

3-Butyl-1-(2-methylpropyl)-4-[[2'-(1H-tetrazol-5-yl)[1,1'-biphenyl]-4-yl ]methyl]-1H-pyrazole-5-carboxaldehyde
T.l.c. dichloromethane: ether: acetic acid (75: 25: 1) Rf. 0.45 n.m.r. (250MHz, CDCl$_3$) δ 0.85–0.93 (9H, t+d), 1.33 (2H,m), 1.55 (2H,m), 2.15 (1H, sept), 2.57 (2H, t), 4.13 (2H, s), 4.27 (2H,d), 7.18 (4H, A'BB'), 7.4 (1H,dd), 7.52–7.62 (2H, m), 8.20 (1H,dd), 9.85 (1H, s).

From the product of Example 29.

EXAMPLE 46

3-Butyl-1-(2-cyclopropylmethyl)-4-[[2'-(1H-tetrazol-5-yl)[1,1'-biphenyl]-4-yl]methyl]-1H-pyrazole-5-carboxaldehyde
m.p. 58°–60° C.
T.l.c. dichloromethane:ether:acetic acid (75:25:1) Rf 0.65
From the product of Example 30.

EXAMPLE 47

3-Butyl-1-cyclobutyl-4-[[2'-(1H-tetrazol-5-yl)[1,1'biphenyl]-4-yl]methyl]-1H-pyrazole-5-carboxaldehyde
T.l.c. System F (95:5) Rf 0.63
IR (CHBr$_3$) 1677 cm$^{-1}$
From the product of Example 32.

EXAMPLE 48

1,3-Dibutyl-4-[[2'-(1H-tetrazol-5-yl)[1,1'-biphenyl]-4-yl]methyl]-1H -pyrazole-5-carboxaldehyde
m.p.50°–53° C.
T.l.c. dichloromethane:ether:acetic acid (75:25:1) Rf 0.71
From the product of Example 36.

EXAMPLE 49

1-(1-Methylethyl)-3-propyl-4-[[2'-(1H-tetrazol-5-yl)[-1,1'-biphenyl]4--yl]methyl]-1H-pyrazole-5-carboxaldehyde
m.p. 48°–50° C.
T.l.c. dichloromethane:ether:acetic acid (80:20:1) Rf 0.73
From the product of Example 40.

EXAMPLE 50

3-Butyl-1-ethyl-4-[[2'-(1H-tetrazol-5-yl) [1,1'-biphenyl]-4yl]methyl]-1H-pyrazole-5-carboxylic acid A solution of sodium chlorite (80%;0.44 g) and sodium dihydrogen phosphate (0.44 g) in water (5 ml) was added to a mixture of the product of Example 27 (203 mg), 2-methyl-2-butene (2M,0.62 ml) and t-butanol (4 ml) in THF (10 ml) at room temperature. The mixture was stirred vigorously for 20 mins. The mixture was partitioned between ethyl acetate (3×15 ml) and water (15 ml). The combined organic extracts were dried. The solvent was evaporated to give a colourless foam (0.2 g) which was purified by column chromatography on silica gel eluting with System G (50:50:1) to give the title compound as a colourless solid (60 mg).
T.l.c. System G (50:50:1) Rf 0.25;
Assay Found: C,66.8; H,6.0; N, 19.4;
$C_{24}H_{26}N_6O_2$ requires: C,67.0; H,6.1; N,19.5%
Similarly prepared:

EXAMPLE 51

3-Butyl-1-(1-methylethyl)-4-[[2'-(1H-tetrazol-5-yl)[1,1'-biphenyl]-4yl ]methyl]-1H-pyrazole-5-carboxylic acid
m.p. 80°–81° C.
T.l.c. dichloromethane:ether:acetic acid (120:10:1) Rf 0.2
From the product of Example 43.

EXAMPLE 52

5-Butyl-1-(1-methylethyl)-4-[[2'-(1H-tetrazol-5-yl)[1,1-biphenyl]-4-yl]methyl]-1H-pyrazole-3-carboxylic acid
m.p. 105°–108° C.
T.l.c. dichloromethane:ether:acetic acid (75:25:1) Rf 0.25
From the product of Example 44.

EXAMPLE 53

3-Butyl-1-(2-methylpropyl)-4-[[2'-(1H-tetrazol-5-yl)[1,1'-biphenyl]-4-yl ]methyl]-1H-pyrazole-5-carboxylic acid
m.p. 178°–182° C.
T.l.c. dichloromethane:ether:acetic acid (75:25:1) Rf 0.5
From the product of Example 45.

EXAMPLE 54

3-Butyl-1-cyclobutyl-4-[[2'-(1H-tetrazol-5-yl) [1,1'-biphenyl]-4-yl]methyl]-1H-pyrazole-5-carboxylic acid
m.p. 103°–106° C.
T.l.c. dichloromethane:ether:acetic acid (175:10:1) Rf 0.13
From the product of Example 47.

EXAMPLE 55

5-[4'-[[3-Butyl-5-(methoxymethyl)-1-phenyl-1H-pyrazol-4-yl]methyl ][1,1'-biphenyl]-2-yl]-1H-tetrazole
Phenylhydrazine and Intermediate 5 were reacted according to the method of Intermediate 18 to give the title compound as a pale yellow foam.
T.l.c. ether:petroleum ether:acetic acid (100:100:1) Rf. 0.2
n.m.r. (250MHz, $CH_3OD$) δ 0.88 (3H,t), 1.30 (2H,m), 1.48 (2H,m), 2.52 (2H,t), 3.28 (3H, s), 3.92 (2H, s), 4.30 (2H, s), 7.1 (4H,dd), 7.4–7.7 (9H,m).

EXAMPLE 56

1,3-Diethyl-4-[[2'-(1H-tetrazol-5-yl) [1,1'-biphenyl]-4-yl]methyl]-1H-pyrazole-5-methanol
From Intermediate 35a according to the method of Example 26.
T.l.c. dichloromethane:methanol (10:1) Rf 0.56
IR (Nujol mull) 3350 & 1494 $cm^{-1}$.

EXAMPLE 57

1,5-Diethyl-4-[[2'-(1H-tetrazol-5-yl)[1,1'-biphenyl]-4-yl]methyl]-1H -pyrazole-3-methanol
From Intermediate 35b according to the method of Example 26.
T.l.c. dichloromethane:methanol (10:1) Rf 0.36
IR (Nujol mull) 3317 & 1494 $cm^{-1}$.

EXAMPLE 58

3-Butyl-4-[(2'-carboxy[1,1'-biphenyl]-4-yl)methyl]-1-ethyl-1H-pyrazole -5-carboxylic acid
From Intermediate 44 according to the method of Example 4.
m.p. 190°–192° C.
T.l.c. ether:hexane:acetic acid (50:50:1) Rf 0.35

EXAMPLE 59

3-Butyl-1-propyl-4-[[2'-(1H-tetrazol-5-yl) [1,1'-biphenyl]-4-yl]methyl]-1H-pyrazole-5-methanol
From Intermediate 28a according to the method of Example 26.
m.p. 79°–82° C.
T.l.c. dichloromethane:methanol (10:1) Rf 0.45

EXAMPLE 60

1-Ethyl-3-propyl-4-[[2'-(1H-tetrazol-5-yl) [1,1'-biphenyl]-4-yl]methyl]-1H-pyrazole-5-carboxaldehyde
From the product of Example 38 according to the method of Example 42.
m.p. 48°–50° C.
T.l.c. dichloromethane:ether:acetic acid (80:20:1) Rf 0.73.

EXAMPLE 61

1-Ethyl-3-propyl-4-[[2'-(1H-tetrazol-5-yl)[1,1'-biphenyl]-4-yl]methyl]-1H-pyrazole-5-carboxylic acid
From the product of Example 60 according to the method of Example 50.
m.p. 118°–123° C.
T.l.c. dichloromethane:ether:acetic acid (80:20:1) Rf 0.45.

EXAMPLE 62

1-(1-Methylethyl)-3-propyl-4-[[2'-(1H-tetrazol-5-yl)[1,1'-biphenyl]-4-yl ]methyl]-1H-pyrazole-5-carboxylic acid
From the product of Example 49 according to the method of Example 50.
m.p. 108°–111° C.
T.l.c. dichloromethane:ether:acetic acid (90:10:1) Rf 0.62.

EXAMPLE 63

1,3-Dibutyl-4-[[2'-(1H-tetrazol-5-yl)[1,1'-biphenyl]-4-yl)methyl]-1H -pyrazole-5-carboxylic acid
From the product of Example 48 according to the method of Example 50.
m.p. 185°–188° C.
T.l.c. dichloromethane:ether:acetic acid (100:5:1) Rf 0.42.

EXAMPLE 64

3-Butyl-4-[(2'-carboxy[1,1'-biphenyl]-4-yl) methyl]-1-(1-methylethyl) -1H-pyrazole-5-carboxylic acid
From the product of Intermediate 46 according to the method of Example 4.
m.p. 213°–215° C.
T.l.c. System G (20:20:1) Rf 0.44
The compounds of the invention are tested in vitro for angiotensin II antagonism. Aortic strips are obtained from male New Zealand white rabbits and prepared for recording isometric contractions in response to cumulative addition of angiotensin II. The potencies of test antagonists are assessed by measuring their abilities to displace the angiotensin II cumulative concentration response curve. The method used is that of Ackerly et al., *Proc. Natl. Acad. Sci.*, 74(12), pp5725–28 (1977) with the exception that the final composition of the physiological salt solution is as given below in Table 1:

TABLE 1

| Ingredient | Amount (mM) |
|---|---|
| $Na^+$ | 143.4 |
| $K^+$ | 5.9 |
| $Mg^{2+}$ | 0.6 |
| $Ca^{2+}$ | 1.3 |
| $Cl^-$ | 124.5 |
| $HPO_4^-$ | 1.2 |
| $SO_4^{2-}$ | 0.6 |
| $HCO_3^-$ | 25.0 |
| glucose | 11.1 |
| indomethacin | 0.005 |
| ascorbic acid | 0.1 |

The tissues are initially challenged with $K^+$ (80 mM) and then washed at 0, 5, 10 and 15 minutes after the response to $K^+$ has plateaued. After a further 45 minutes an angiotensin II cumulative response curve is constructed (0.1 nM to 0.1 μM in 10-fold increments) and the tissues are washed as before. A second, third and fourth angiotensin II cumulative response curve (0.1 nM to 0.1 μM in 3-fold increments) is then constructed at hourly intervals (15 minutes washing after each curve followed by 45 minutes equilibration). The compounds of the invention (30 μM) are tested for angiotensin II antagonism by application 45 minutes before construction of the fourth angiotensin II curve. The third and fourth angiotensin II curves are expressed graphically and a concentration ratio (CR) is calculated by dividing the angiotensin II $EC_{50}$ value obtained in the presence of the test antagonist (i.e. fourth curve) by the angiotensin II $EC_{50}$ value obtained in the absence of the test antagonist (i.e. third curve).

The potency of the test antagonist is expressed as a pKb which is calculated from the equation:

$$pKb = -\log\left[\frac{CR-1}{[\text{antagonist}]}\right]$$

which is a rearrangement of equation 4 described by Furchgott, in *Handbook of Exp. Pharmacol.*, 33, p290 (1972) (eds. Blaschkott and Muscholl).

Compounds of the invention will desirably exhibit a pKb in the range between 5 and 12. Thus we have found that the compounds of the invention inhibit the action of the hormone angiotensin II and are therefore useful in the treatment of conditions in which it is desirable to inhibit angiotensin II activity. In particular, the compounds of Examples are active in the above test.

There is thus provided as a further aspect of the invention a compound of general formula (I) or a physiologically acceptable salt, solvate or metabolically labile ester thereof for use in the treatment of conditions associated with excessive or unregulated angiotensin II activity.

In a further or alternative aspect of the invention there is provided a compound of general formula (I) or a physiologically acceptable salt, solvate or metabolically labile ester thereof for the manufacture of a therapeutic agent for the treatment of conditions associated with excessive or unregulated angiotensin II activity.

There is also provided in a further or alternative aspect of the invention a method for the treatment of conditions associated with excessive or unregulated angiotensin II activity in a mammal including man comprising administration of an effective amount to a mammal in need of such treatment a compound of general formula (I) or a physiologically acceptable salt, solvate or metabolically labile ester thereof.

The following examples illustrate pharmaceutical formulations according to the invention. The term "active ingredient" is used herein to represent a compound of formula (I).

PHARMACEUTICAL EXAMPLE 1

| Oral Tablet A | |
|---|---|
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled in the art. Pigments may be incorporated in the film coat.

PHARMACEUTICAL EXAMPLE 2

| Oral Tablet B | |
|---|---|
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

PHARMACEUTICAL EXAMPLE 3

| Inhalation Cartridge | |
|---|---|
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

PHARMACEUTICAL EXAMPLE 4

| Injection Formulation | |
| --- | --- |
| | % w/v |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

The present invention is further illustrated by the following Examples:

INTERMEDIATES 47a AND b (a) 5-[4'-[[1-(2,2-Dimethylpropyl)-3-propyl-5-[(phenylmethoxy) methyl]-1H-pyrazol-44-yl]methyl][1,1'-biphenyl]-2-yl]-2-(triphenylmethyl)-2H-tetrazole; and (b) 5-[4'-[[1-(2,2-Dimethylpropyl)-5-propyl-3-[(phenylmethoxy) methyl]-1H-pyrazol-4-yl]methyl][1,1'-biphenyl]-2-yl]-2-(triphenylmethyl)-2H-tetrazole From Intermediate 21 and 2,2-dimethylpropyl iodide according to the method of Intermediate 22.

Intermediate 47a: T.l.c. System A (1:2) Rf 0.29
Intermediate 47b: T.l.c. System A (1:2) Rf 0.21

INTERMEDIATES 48a AND b (a) 5-[4'-[[3-Butyl-5-methoxymethyl-1-(prop-2-enyl)-1H-pyrazol-4-yl]methyl][1,1'-biphenyl]-2-yl]-2-(triphenylmethyl)-2H-tetrazole; and (b) 5-[4'-[[5-Butyl-3-methoxymethyl-1-(prop-2-enyl)-1H-pyrazol-4-yl]methyl][1,1'-biphenyl]-2-yl]-2-(triphenylmethyl)-2H -tetrazole A solution of Intermediate 9 (2.5 g) in DMF (10 ml) was added dropwise to a suspension of sodium hydride (60% dispersion in oil, 0.22 g) in DMF (5 ml) at 0° C. under nitrogen. 3-Bromopropene (0.46 g) was added to the stirred mixture and stirring continued at room temperature for 3 hours. The solvent was removed in vacuo and the residue purified by column chromatography eluting with System A (4:3) to give the title compound:

(a) Intermediate 48a as a white foam (860 mg), T.l.c. System A (2:1) Rf 0.50

(b) Intermediate 48b as a white foam (101 mg), T.l.c. System A (2:1) Rf 0.25

INTERMEDIATES 49a AND b (a) 1,1-Dimethylethyl 4'-[[3-butyl-1-methyl-5-[(phenylmethoxy) methyl]-1H-pyrazol-4-yl]methyl][1,1'-biphenyl]-2-carboxylate; and (b) 1,1-Dimethylethyl 4'-[[5-butyl-1-methyl-3-[(phenylmethoxy) methyl]-1H-pyrazol-4-yl]methyl][1,1'-biphenyl]-2-carboxylate From Intermediate 37 and methyl iodide according to the method of Intermediate 22.

Intermediate 49a: T.l.c. System A (1:1) Rf 0.15
Intermediate 49b: T.l.c. System A (1:1) Rf 0.10

INTERMEDIATE 50

1,1-Dimethylethyl 4'-[[3-butyl-5-(hydroxymethyl)-1-methyl-1H-pyrazol-4-yl]methyl][1,1'-biphenyl]-2-carboxylate From Intermediate 49a according to the method of Example 26.

T.l.c. System D (1:1) Rf 0.1

INTERMEDIATE 51

1,1-Dimethylethyl 4'-[[3-butyl-5-formyl-1-methyl-1H-myrazol-4-yl]methyl][1,1'-biphenyl]-2-carboxylate From Intermediate 50 according to the method of Example 42.

T.l.c. System D (1:1) Rf 0.3

INTERMEDIATE 52

3-Butyl-4-[[2'-[(1,1-dimethylethoxy)carbonyl][1,1'-biphenyl]-4-yl]methyl]-1-methyl-1H-pyrazole-5-carboxylic acid From Intermediate 51 according to the method of Example 50.

m.p. 117°-118° C.

INTERMEDIATE 53

3-[(2'-Nitro[1,1'-biphenyl]-4-yl)methyl]-1-(phenylmethoxy)-2,4-octandione

From Intermediate 19 and 4'-(bromomethyl)-2-nitro-1,1'-biphenyl according to the method of Intermediate 17.

T.l.c. System A (1:1) Rf 0.6

INTERMEDIATE 54

3-[(2'-Nitro[1,1'-biphenyl]-4-yl)methyl]-1-(phenylmethoxy)-2,4-octandione

From Intermediate 16 and 4'-(bromomethyl)-2-nitro-1,1'-biphenyl according to the method of Intermediate 17.

T.l.c. System A (1:5) Rf 0.4

INTERMEDIATE 55

4-[(2'-Nitro[1,1'-biphenyl]-4-yl)methyl]-5-[(phenylmethoxy)methyl]-3-propyl-1H-pyrazole From Intermediate 53 and hydrazine hydrate according to the method of Intermediate 18.

T.l.c. System B (300:8:1) Rf 0.28

INTERMEDIATE 56

3-Butyl-4-[(2'-nitro[1,1'-biphenyl]-4-yl)methyl]-5-[(phenylmethoxy) methyl]-1H-pyrazole From Intermediate 54 and hydrazine hydrate according to the method of Intermediate 18.

T.l.c. System B (400:8:1) Rf 0.5

INTERMEDIATES 57a AND b (a) 1-Ethyl-4-[(2'-nitro[1,1'-biphenyl]-4-yl)methyl]-5-[(phenylmethoxy) methyl]-3-propyl-1H-pyrazole; and (b) 1-Ethyl-4-[(2'-nitro[1,1'-biphenyl]-4-yl)methyl]-3-[(phenylmethoxy) methyl]-5-propyl-1H-pyrazole From Intermediate 55 and ethyl iodide according to the method of Intermediate 22.

Intermediate 57a: T.l.c. System A (1:1) Rf 0.2
Intermediate 57b: T.l.c. System A (1:1) Rf 0.12

INTERMEDIATES 58a AND b (a) 3-Butyl-1-ethyl-4-[(2'-nitro[1,1'-bipbenyl]-4-yl)methyl]-5-[(phenylmethoxy) methyl]-1H-pyrazole; and (b) 5-Butyl-1-ethyl-4-[(2'-nitro[1,1'-bipbenyl]-4-yl)methyl]-3-[(phenylmethoxy) methyl]-1H-pyrazole From Intermediate 56 and ethyl iodide according to the method of Intermediate 22.

Intermediate 58a: T.l.c. System A (1:1) Rf 0.22
Intermediate 58b: T.l.c. System A (1:1) Rf 0.11

INTERMEDIATE 59

4'-[[1-Ethyl-5-[(phenylmethoxy)methyl]-3-propyl-1H-pyrazol-4-yl]methyl][1,1'-biphenyl]-2-amine Titanium trichloride solution (15% w/v, 33 ml) was added to a solution of Intermediate 57a (1.5 g) in acetone (30 ml) and the resulting mixture stirred overnight. Further titanium trichloride solution (10 ml) was added and the reaction warmed to 40° C. for 16 h. 2N Sodium carbonate (200 ml) was added and the mixture extracted with dichloromethane (3×150 ml). The combined, dried, organic extracts were evaporated in vacuo and the residue purified by chromatography eluting with System A (2:1) to give the title compound as a yellow coloured oil (1.03 g).

T.l.c. System A (4:1), Rf 0.36
Similarly prepared:

INTERMEDIATE 60

4'-[[3-Butyl-1-ethyl-5-[(phenylmethoxy)methyl]-1H-pyrazol-4-yl]methyl][1,1'-biphenyl]-2-amine
T.l.c. System A (2:1) Rf 0.28
From Intermediate 58a.

INTERMEDIATE 61

N-[4'-[[1-Ethyl-5-[(phenylmethoxy)methyl]-3-propyl-1H-pyrazol-4-yl]methyl][1,1'-biphenyl]-2-yl]trifluoromethanesulphonamide A solution of Intermediate 59 (1 g) and triethylamine (0.35 ml) in dry dichloromethane (20 ml) at −70° C. was treated dropwise with a solution of triflic anhydride (0.46 ml) in dichloromethane (5 ml) and the resulting mixture stirred at −70° C. for 1 h. Water (10 ml) was added and the reaction allowed to warm to room temperature. The aqueous layer was separated and the organic washed with 2N hydrochloric acid (10 ml). The dried organic solution was evaporated in vacuo and the residue purified by chromatography eluting with System B (300:8:1) to give the title compound as a foam (0.93 g).

T.l.c. System B (100:8:1), Rf 0.31
Similarly prepared:

INTERMEDIATE 62

N-[4'-[[3-Butyl-1-ethyl-5-[(phenylmethoxy)methyl]-1H-pyrazol-4-yl]methyl][1,1'-biphenyl]-2-yl]trifluoromethane-sulphonamide
T.l.c. System B (150:8:1) Rf 0.15
From Intermediate 60.

Examples 65 to 71 inclusive were prepared according the method of Example 26:

EXAMPLE 65

5-Butyl-1-(2-methylpropyl)-4-[[2'-(1H-tetrazol-5-yl)[1,1'-biphenyl]-4-yl]methyl]-1H-pyrazole-3-methanol
m.p. 65°–68° C.
T.l.c. dichloromethane:ether:acetic acid (75:25:1) Rf 0.15
From Intermediate 24b.

EXAMPLE 66

5-Butyl-1-(2-cyclopropytmethyl)-4-[[2'-(1H-tetrazol-5-yl)[1,1-biphenyl]-4-yl]biphenyl]-4-yl]methyl]-1H-pyrazole-3-methanol
m.p. 70°–75° C.
T.l.c. dichloromethane:ether:acetic acid (75:25:1) Rf 0.15
From Intermediate 25b.

EXAMPLE 67

5-Butyl-1-propyl-4-[[2'-(1H-tetrazol-5-yl) [1,1'-biphenyl]-4-yl]methyl]-1H-pyrazole-3-methanol
m.p. 59°–62° C.
T.l.c. dichloromethane:methanol (10:1) Rf 0.41
From Intermediate 28b.

EXAMPLE 68

1-(2-Methylpropyl)-3-propyl-4-[[2'-(1H-tetrazol-5-yl)[1,1'-biphenyl]-4-yl]methyl]-1H-pyrazole-5-methanol
m.p. 104°–108° C.
T.l.c. dichloromethane:methanol (10:1) Rf 0.7
From Intermediate 45a.

EXAMPLE 69

1-(2-Methylpropyl)-5-propyl-4-[[2'-(1H-tetrazol-5-yl)[1,1'-biphenyl]-4-yl]methyl]-1H-pyrazole-3-methanol
m.p. 55°–61° C.
T.l.c. dichloromethane:methanol (10:1) Rf 0.57
From Intermediate 45b.

EXAMPLE 70

1-(2,2-Dimethylpropyl)-3-propyl-4-[[2'-(1H-tetrazol-5-yl) [1,1'-biphenyl]-4-yl]methyl]-1H-pyrazole-5-methanol
m.p. 79°–80° C.
T.l.c. dichloromethane:ether:acetic acid (90:10:1) Rf 0.3
From Intermediate 47a.

EXAMPLE 71

1-(2,2-Dimethylpropyl)-5-propyl-4-[[2'-(1H-tetrazol-5-yl)[1,1'-biphenyl]-4-yl]methyl]-1H-pyrazole-3-methanol
m.p. 136°–139° C.
T.l.c. dichloromethane:ether:acetic acid (90:10:1) Rf 0.28
From Intermediate 47b.

Examples 72 to 75 inclusive were prepared according to the method of Example 42:

EXAMPLE 72

3-Butyl-1-methyl-4-[[2'-(1H-tetrazol-5-yl) [1,1'-biphenyl]-4-yl]methyl]-1H-pyrazole-5-carboxaldehyde
m.p. 53°–56° C.
T.l.c. dichloromethane:ether:acetic acid (90:10:1) Rf 0.3
From the product of Example 34.

EXAMPLE 73

3-Butyl-1-propyl-4-[[2'-(1H-tetrazol-5-yl) [1,1'-biphenyl]-4-yl]methyl]-1H-pyrazole-5-carboxaldehyde
m.p. 48°–50° C.
T.l.c. dichloromethane:ether:acetic acid (75:25:1) Rf 0.68

From the product of Example 59.

EXAMPLE 74

1-(2-Methylpropyl)-3-propyl-4-[[2'-(1H-tetrazol-5-yl)[1,1'-biphenyl]-4-yl]methyl]-1H-pyrazole-5-carboxaldehyde m.p. 54°–56° C.

T.l.c. dichloromethane:ether:acetic acid (90:10:1) Rf 0.57

From the product of Example 68.

EXAMPLE 75

1-(2,2-Dimethylpropyl)-3-propyl-4-[[2'-(1H-tetrazol-5-yl)[1,1'-biphenyl]-4-yl]methyl]-1H-pyrazole-5-carboxaldehyde m.p. 60°–62° C.

T.l.c. dichloromethane:ether:acetic acid (90:10:1) Rf 0.46

From the product of Example 70.

Examples 76 to 80 inclusive were prepared according to the method of Example 50:

EXAMPLE 76

3-Butyl-1-(2-cyclopropylmethyl)-4-[[2'-(1H-tetrazol-5-yl)[1,1'-biphenyl]-4-yl]methyl]-1H-pyrazole-5-carboxylic acid m.p. 205°–206° C.

T.l.c. dichloromethane:ether:acetic acid (72:25:1) Rf 0.5

From the product of Example 46.

EXAMPLE 77

3-Butyl-1-methyl-4-[[2'-(1H-tetrazol-5-yl)[1,1-biphenyl]-4-yl]methyl]-1H-pyrazole-5-carboxylic acid m.p. 118°–122° C.

T.l.c. dichloromethane:ether:acetic acid (90:10:1) Rf 0.23

From the product of Example 72.

EXAMPLE 78

3-Butyl-1-propyl-4-[[2'-(1H-tetrazol-5-yl) [1,1'-biphenyl]-4-yl]methyl]-1H-pyrazole-5-carboxylic acid m.p. 181°–183° C.

T.l.c. dichloromethane:ether:acetic acid (90:10:1) Rf 0.36

From the product of Example 73.

EXAMPLE 79

1-(2-Methylpropyl)-3-propyl-4-[[2'-(1H-tetrazol-5-yl)[1,1'-biphenyl]-4-yl]methyl]-1H-pyrazole-5-carboxylic acid m.p. 138°–140° C.

T.l.c. dichloromethane:ether:acetic acid (90:10:1) Rf 0.22

From the product of Example 74.

EXAMPLE 80

1-(2,2-Dimethylpropyl)-3-propyl-4-[[2'-(1H-tetrazol-5-yl)[1,1'-bipbenyl]-4-yl]methyl]-1H-pyrazole-5-carboxylic acid m.p. 122°–126° C.

T.l.c. dichloromethane:ether:acetic acid (95:5:1) Rf 0.3

From the product of Example 75.

EXAMPLE 81

5-[4'-[[5-Butyl-3-methoxymethyl-1-(1,1'-dimethylethyl)-1H-pyrazol-4-yl]methyl][1,1'-biphenyl]-2-yl]-1H-tetrazole A solution of Intermediate 5 (5 g), 1,1-dimethylethylhydrazine hydrochloride (959 mg) and triethylamine (1.11 ml) in ethanol (50m) was heated at 60° C. for 6 h after which time additional triethylamine (2.22 ml) and 1,1-dimethylethylhydrazine hydrochloride (1.92 g) were added and the resultant mixture stirred at 60° C. for a further 18 h and then at room temperature for 24 h. The solvents were removed in vacuo and the residue purified by column chromatography eluting with petroleum ether:ether (2:1) initially followed by ethanol. The concentrated ethanolic extracts were further purified by column chromatography eluting with System B (100:5:1) to give the title compound(746 mg) as a cream coloured foam.

mp 58°–60° C.

EXAMPLE 82

1,5-Dibutyl-4-[[2'-(1H-tetrazol-5-yl) [1,1-biphenyl]-4-yl]methyl]-1H -pyrazole-3-carboxylic acid A solution of potassium permanganate (55 mg) in water (3 ml) was added to a stirred solution of the product of Example 37 (140 mg) in acetone (3 ml) at 50° C. The resulting mixture was stirred at 65° C. for 1½ hours. A further portion of potassium permanganate (55 mg) was added and the mixture stirred for 3 hours. Sodium metabisulphite (5% w/v, 15 ml) was added and the aqueous phase was extracted with ethyl acetate (3×30 ml). The combined organic extracts were dried and concentrated to yield a white foam which was purified by column chromatography, eluting with ether/dichloromethane (1:1) to yield the title compound as a white solid (70 mg).

m.p. 108° C.

EXAMPLE 83

5-[4'-[[3-Butyl-5-methoxymethyl-1-(prop-2-enyl)-1H-pyrazol-4-yl]methyl][1,1'-biphenyl]-2-yl]-1H-tetrazole A solution of Intermediate 48a (800 mg), methanol (15 ml) and concentrated hydrochloric acid (0.5 ml) was stirred at room temperature for 3 hours. The pH of the solution was adjusted to pH9 (2N NaCO₃) and the solvent removed in vacuo. The residue was partitioned between water (20 ml) and ether (3×20 ml). The aqueous layer was then acidified to pH3 (2NHCl) and extracted into ethyl acetate (3×20 ml). The ethyl acetate fractions were combined, dried and the solvent removed in vacuo to afford the title compound as a white foam (470 mg). m.p. 39°–41° C.

T.l.C. ether Rf 0.40

Similarly prepared:

EXAMPLE 84

5-[4'-[[5-Butyl-3-methoxymethyl-1-(prop-2-enyl)-1H-pyrazol-4-yl]methyl][1,1'-biphenyl]-2-yl]-1H-tetrazole as a white foam (600 mg). m.p. 37°–40° C.

T.l.c. ether Rf 0.24

From a solution of Intermediate 48b (1.00 g), methanol (15 ml) and concentrated hydrochloric acid (0.5 ml).

EXAMPLE 85

3-Butyl-4-[(2'carboxy[1,1'-biphenyl]-4-yl)methyl]-1-methyl-1H-pyrazole -5-carboxylic acid From Intermediate 52 according to the method of Example 4.
m.p. 168°-170° C.
Analysis Found C,70.2; H, 6.3; N, 6.8;
$C_{23}H_{24}N_2O_4$ requires C,70.4; H,6.2; N,7.1%

EXAMPLE 86

N-[4'-[[1-Ethyl-5-(hydroxymethyl)-3-propyl-1H-pyrazol-4-yl]methyl][1,1'-biphenyl]-2-yl]trifluoromethanesulphonamide A solution of Intermediate 61 (0.89 g) in absolute ethanol (25 ml) and 2N hydrochloric acid (0.7 ml) was hydrogenated with 10% palladium on carbon catalyst (0.6 g) for 1½ h. The reaction was filtered into a flask containing 2N sodium carbonate solution (0.7 ml) and the solvent removed in vacuo. The residue was taken up in dichloromethane (15 ml) and washed with water (15 ml). The organic solution was dried and evaporated in vacuo to give the title compound as a white foam (0.65 g) m.p. 59°-64° C.
T.l.c. System A Rf 0.19
Similarly prepared:

EXAMPLE 87

N-[4'-[[3-Butyl-1-ethyl-5-(hydroxymethyl)-1H-pyrazol-4-yl]methyl][1,1'-biphenyl]-2-yl]trifluoromethanesulphonamide
T.l.c System B (150:8:1) Rf 0.12
Analysis Found C, 57.8; H, 6.1: N, 8.2;
$C_{24}H_{28}N_3O_3$ requires C,58.2; H, 5.7; N,8.5%
From Intermediate 62.

EXAMPLE 88

N-[4'-[[1-Ethyl-5-formyl-3-propyl-1H-pyrazol-4-yl]methyl][1,1'-biphenyl]-2-yl]trifluoromethanesulphonamide Tetra-n-propylammonium perruthenate (46 mg) was added to a mixture of the product of Example 86 (630 mg), N-methylmorpholine N-oxide (0.46 g) and 4A molecular sieves (2.5 g) in dichloromethane (10 ml) and dry acetonitrile (10 ml) and the reaction left for 5 min. The reaction was filtered, solvent removed in vacuo and the residue adsorbed onto silica. The material was purified by chromatography eluting with System A (4:1) to give the title compound as a yellow gum (0.44 g).
T.l.c. System A (4:1), Rf 0.64
I.r. (CHBr$_3$) 1679, 1597, 1366 cm$^{-1}$.
Similarly prepared:

EXAMPLE 89

N-[4'-[[3-Butyl-1-ethyl-5-formyl-1H-pyrazol-4-yl]methyl][1,1'-biphenyl]-2-yl]trifluoromethanesulphonamide
T.l.c. System A (3:1 ) Rf 0.56
n.m.r. (CDCl$_3$, 250 MHz) δ 0.94 (3H, t), 1.44 (3H,t), 1.62 (2H,m), 2.55 (2H, t), 4.15 (2H,s), 4.54 (2H, quad), 7.25-7.45 (7H,m), 7.64 (1H,m), 9.9 (1H, s).
From the product of Example 87.

EXAMPLE 90

1-Ethyl-3-propyl-4-[[2'-[[(trifluoromethyl)sulphonyl]amino][1,1'-biphenyl]-4-yl]methyl]-1H-pyrazole-5-carboxylic acid A solution of sodium chlorite (0.4 g) and sodium dihydrogen orthophosphate (2.56 g) in water (5 ml) was added to a solution of the product of Example 88 (430 mg) and 2-methyl-2-butene (4.5 ml, 2M solution in THF) in t-butanol (5 ml) and THF (10 ml) and the resulting mixture stirred for 3 h. Solvent was removed in vacuo, the residue taken up in dichloromethane (10 ml) and washed with water (10 ml). 2N Sodium hydroxide (10 ml) was added to the organic solution and the organic layer removed. 2N Hydrochloric acid (~11 ml) was added to the aqueous phase which was then extracted with ethyl acetate (2×15 ml). The dried organic extracts were evaporated in vacuo to give a yellow gummy solid which was recrystaltised from System D (1:1) to give the title compound as a white solid (250 mg) m.p. 68°-72° C.
T.l.c. System A (2:1), Rf 0.53
Similarly prepared:

EXAMPLE 91

3-Butyl-1-ethyl-4-[[2'-[[(trifluoromethyl)sulphonyl]amino][1,1'-biphenyl]-4-yl]methyl]-1H-pyrazole-5-carboxylic acid
T.l.c. System G (300:100:4) Rf 0.55
n.m.r. (CDCl$_3$, 250 MHz) δ 0.87 (3H,t), 1.32 (2H, m), 1.44 (3H,t), 1.55 (2H,m), 2.56 (2H, t), 4.18 (2H,s), 4.58 (2H,q), 6.67 (1H,br.s), 7.17-7.3 (7H,m), 7.37 (1H,dt), 7.61 (1H,br.d).
From the product of Example 89.

We claim:

1. A compound of formula (I)

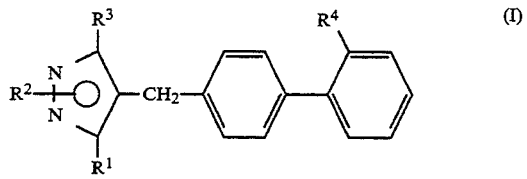

or a physiologically acceptable salt, solvate or a metabolically labile ester thereof wherein $R^1$ represents a hydrogen atom or a group selected from $C_{1-6}$alkyl or $C_{2-6}$alkenyl;

$R^2$ represents a hydrogen atom or a group selected from $C_{1-6}$alkyl, $C_{3-7}$cycloalkyl, $C_{3-7}$cycloalkyl$C_{1-4}$alkyl, $C_{3-6}$alkenyl, fluoro$C_{1-6}$alkyl, fluoro$C_{3-6}$alkenyl, phenyl, —(CH$_2$)$_k$CO R$^5$ or —(CH$_2$)$_k$SO$_2$R$^5$;

$R^3$ represents —(CH$_2$)$_n$COR$^7$;

$R^4$ represents a C-linked tetrazolyl group;

$R^5$ represents a group selected from $C_{1-6}$alkyl, $C_{2-6}$alkenyl, $C_{1-6}$alkoxy or the group —NR$^{10}$R$^{11}$;

$R^7$ represents a group selected from hydroxy, $C_{1-6}$alkoxy or phenoxy;

$R^{10}$ and $R^{11}$ which may be the same or different each independently represent a hydrogen atom or a $C_{1-4}$alkyl group or —NR$^{10}$R$^{11}$ forms a saturated heterocyclic ring which has 5 or 6 ring members and may optionally contain in the ring one oxygen atom;

k represents zero or an integer from 1 to 4; and,
n represents zero.

2. A compound of formula (I)

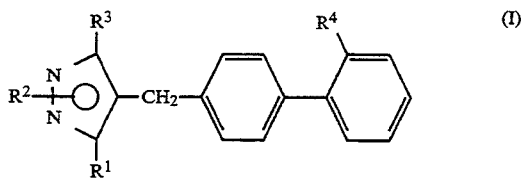

or a physiologically acceptable salt, solvate or a metabolically labile ester thereof wherein $R^1$ represents a group selected from $C_{1-6}$alkyl or $C_{2-6}$alkenyl;

$R^2$ represents a hydrogen atom or a group selected from $C_{1-6}$alkyl, $C_{3-6}$alkenyl, fluoro$C_{1-6}$alkyl, fluoro$C_{3-6}$alkenyl, phenyl, —$(CH_2)_kCOR^5$ or —$(CH_2)_kSO_2R^5$;

$R^3$ represents —$(CH_2)_nCOR^7$;

$R^4$ represents a C-linked tetrazolyl group;

$R^5$ represents a group selected from $C_{1-6}$alkyl, $C_{2-6}$alkenyl, $C_{1-6}$alkoxy or the group —$NR^{10}R^{11}$;

$R^7$ represents a group selected from hydroxy, $C_{1-6}$alkoxy or phenoxy;

$R^{10}$ and $R^{11}$ which may be the same or different each independently represent a hydrogen atom or a $C_{1-4}$alkyl group or —$NR^{10}R^{11}$ forms a saturated heterocyclic ring which has 5 or 6 ring members and may optionally contain in the ring one oxygen atom;

k represents zero or an integer from 1 to 4; and
n represents zero.

3. A compound of formula (I)

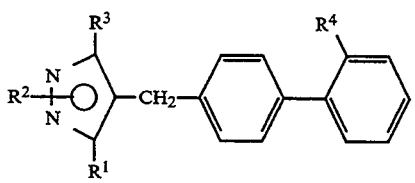

or a physiologically acceptable salt, solvate or a metabolically labile ester thereof wherein $R^1$ represents a group selected from $C_{1-6}$alkyl or $C_{2-6}$alkenyl;

$R^2$ represents a hydrogen atom or a group selected from $C_{1-6}$alkyl, $C_{3-6}$alkenyl, fluoro$C_{1-6}$alkyl, fluoro$C_{3-6}$alkenyl, —$(CH_2)_kCOR^5$ or —$(CH_2)_kSO_2R^5$;

$R^3$ represents —$(CH_2)_nCOR^7$;

$R^4$ represents a C-linked tetrazolyl group;

$R^5$ represents a group selected from $C_{1-6}$alkyl, $C_{2-6}$alkenyl, $C_{1-6}$alkoxy or the group —$NR^{10}R^{11}$;

$R^7$ represents a group selected from hydroxy, $C_{1-6}$alkoxy or phenoxy;

$R^{10}$ and $R^{11}$ which may be the same or different each independently represent a hydrogen atom or a $C_{1-4}$alkyl group or $NR^{10}R^{11}$ forms a saturated heterocyclic ring which has 5 or 6 ring members and may optionally contain in the ring one oxygen atom;

k represents zero or an integer from 1 to 4; and
n represents zero.

4. A compound selected from:
3-butyl-1-(1-methylethyl)-4-[[2'(1H-tetrazol-5-yl)[1,1'-biphenyl]-4-yl ]-1H-pyrazole-5-carboxylic acid;
3-butyl-1-(2-methylpropyl)-4-[[2'-(1H-tetrazol-5-yl)[1,1'-biphenyl]-4-yl methyl]-1H-pyrazole-5-carboxylic acid;
3-butyl-1-cyclobutyl-4-[[2'-(1H-tetrazol-5-yl)[1,1'-biphenyl]-4-yl]methyl -1H-pyrazole-5-carboxylic acid;
1-ethyl-3-propyl-4-[[2'-(1H-tetrazol-5-yl)[1,1'-biphenyl]-4-yl]methyl]-1H-pyrazole-5-carboxylic acid;
1-(1-methylethyl)-3-propyl-4-[[2'-(1H-tetrazol-5-yl)[1,1'-biphenyl]-4-yl]methyl]-1H-pyrazole-5-carboxylic acid;
1,3-dibutyl-4-[[2'-(1H-tetrazol-5-yl)[1,1'-biphenyl]-4-yl]methyl]-1H pyrazole-5-carboxylic acid
1-(2-methylpropyl)-3-propyl-4-[[2'-(1H-tetrazol-5-yl)[1,1'-biphenyl]-4-yl]methyl]-1H-pyrazole-5-carboxylic acid;
3-butyl-1-propyl-4-[[2'-(1H-tetrazol-5-yl)[1,1'biphenyl]-4-yl]methyl]-1H-pyrazole-5-carboxylic acid;
3-butyl-1-ethyl-4-[[2'-(1H-tetrazol-5-yl)[1,1'-biphenyl]-4-yl]methyl]-1H-pyrazole-5-carboxylic acid;
3-butyl-1-(2-cyclopropylmethyl)-4-[[2'-(1H-tetrazol-5-yl)[1,1'-biphenyl]-4 -yl]methyl]-1H-pyrazole-5-carboxylic acid;

or a physiologically acceptable salt, solvate or metabolically labile ester thereof.

5. A compound according to claim 1, wherein k represents zero, 1 or 2.

6. A compound according to claim 1 wherein k represents zero or 1.

7. A compound according to claim 1 wherein $R^1$ represents a $C_{1-5}$alkyl group.

8. A compound according to claim 7 wherein $R^1$ represents an ethyl, n-propyl or n-butyl group.

9. A compound according to claim 7 wherein $R^1$ represents a $C_{3-5}$alkyl group.

10. A compound according to claim 9 wherein $R^1$ represents an n-propyl or n-butyl group.

11. A compound according to claim 1 wherein $R^1$ represents a $C_{3-5}$alkenyl group.

12. A compound according to claim 11 wherein $R^1$ represents a prop-1-enyl or but-1-enyl group.

13. A compound according to claim 1 wherein $R^2$ represents a group selected from fluoro$C_{1-6}$alkyl or —$(CH_2)_kSO_2R^5$.

14. A compound according to claim 13 wherein $R^2$ represents a fluoro$C_{1-3}$alkyl group.

15. A compound according to claim 14 wherein $R^2$ represents the group —$CH_2CF_3$.

16. A compound according to claim 13 wherein $R^5$ represents the group —$NR^{10}R^{11}$, where $R^{10}$ and $R^{11}$ each represent a $C_{1-4}$alkyl group.

17. A compound according to claim 16 wherein $R^2$ represents the group —$SO_2N(CH_3)_2$.

18. A compound according to claim 1 wherein $R^2$ represents a group selected from $C_{1-6}$alkyl, $C_{3-7}$cycloalkyl, $C_{3-7}$cycloalkyl$C_{1-4}$alkyl or phenyl.

19. A compound according to claim 19 wherein $R^2$ represents a $C_{1-5}$alkyl group.

20. A compound according to claim 19 wherein $R^2$ represents an ethyl, an isopropyl or an isobutyl group.

21. A compound according to claim 18 wherein $R^2$ represents a $C_{3-5}$cycloalkyl group.

22. A compound according to claim 21 wherein $R^2$ represents a cyclobutyl group.

23. A compound according to claim 18 wherein $R^2$ represents a $C_{3-5}$cycloalkyl$C_{1-4}$alkyl group.

24. A compound according to claim 23 wherein $R^2$ represents a cyclopropylmethyl group.

25. A compound according to claim 1 wherein the group $R^2$ is adjacent to the group $R^3$.

26. A compound according to claim 1 wherein $R^7$ represents a hydroxy or $C_{1-3}$alkoxy group.

27. A compound according to claim 26 wherein the $C_{1-3}$alkoxy group is a methoxy group.

28. A compound according to claim 1 wherein $R^3$ represents the group —$CO_2H$.

29. A compound of formula (I)

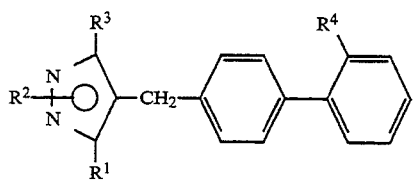

or a physiologically acceptable salt, solvate or metabolically labile ester thereof wherein $R^1$ represents a $C_{1-6}$alkyl group;

$R^2$ represents a hydrogen atom or group selected from $C_{1-6}$alkyl, $C_{3-7}$cycloalkyl, $C_{3-7}$cycloalkyl$C_{1-4}$alkyl, fluoro$C_{1-6}$alkyl, phenyl, —$(CH_2)_kCOR^5$ or —$(CH_2)_kSO_2R^5$;

$R^3$ represents —$(CH_2)_nCOR^7$;

$R^4$ represents a C-linked tetrazolyl group;

$R^5$ represents the group $NR^{10}R^{11}$;

$R^7$ represents a hydroxy group;

$R^{10}$ and $R^{11}$ each independently represent a hydrogen atom or a $C_{1-4}$alkyl group;

k represents zero or an integer from 1 to 4;

n represents zero.

30. A pharmaceutical composition comprising at least one compound of formula (I) as defined in claim 1 or a physiologically acceptable salt, solvate or metabolically labile ester thereof, together with at least one physiologically acceptable carrier or excipient.

31. A method for the treatment or prophylaxis of hypertension which comprises administering to a patient in need of such treatment an effective amount of a compound of formula (I) as defined in claim 1, or a physiologically acceptable salt, solvate or metabolically labile ester thereof.

32. A compound according to claim 31 which is 3-butyl-1-(1-methylethyl)-4-[[2'-(1H -tetrazol-5-yl)[1,1'-biphenyl]-4-yl]methyl-1H-pyrazole-5-carboxylic acid or a physiologically acceptable salt or solvate thereof.

33. A compound according to claim 4 which is 1,3-dibutyl-4-[[2'-(1H-tetrazol-5-yl) [1,1'-biphenyl]-4-yl]methyl]-1H-pyrazole-5-carboxylic acid or a physiologically acceptable salt or solvate thereof.

34. A compound according to claim 4 which is 3-butyl-1-(2-cyclopropylmethyl) -4-[[2'-1H-tetrazol-5-yl)[1,1'-biphenyl]-4-yl]methyl]-1H-pyrazol acid or a physiologically acceptable salt or solvate thereof.

35. A pharmaceutical composition as claimed in claim 30 wherein the compound of formula (I) is 3-butyl-1-(1-methylethyl)-4-[[2'-(1H-tetrazol-5-yl)[1,1'-biphenyl ]-4-yl]methyl-1H-pyrazole-5-carboxylic acid or a physiologically acceptable salt or solvate thereof, together with at least one physiologically acceptable carrier or excipient.

36. A pharmaceutical composition as claimed in claim 30 wherein the compound of formula (I) is 1,3-dibutyl-4-[[2'-(1H-tetrazol-5-yl)[1,1'-biphenyl]-4-yl]methyl]-1H-pyrazole-5-carboxylic acid or a physiologically acceptable salt or solvate thereof, together with at least one physiologically acceptable carrier or excipient.

37. A pharmaceutical composition as claimed in claim 30 wherein the compound of formula (I) is 3-butyl-1-(2-cyclopropylmethyl)-4-[[2'-1H-tetrazol-5-yl)[1,1'biphenyl]-4-yl]methyl]-1H-pyrazole-5-carboxylic acid or a physiologically acceptable salt or solvate thereof, together with at least one physiologically acceptable carrier or excipient.

38. A method according to claim 31 wherein the compound of formula (I) is 3-butyl -1-(1-methylethyl)-4-[[2'-(1H-tetrazol-5-yl)[1,1'-biphenyl]-4-yl]methyl-1H-pyrazole-5-carboxylic acid.

39. A method according to claim 31 wherein the compound of formula (I) is 1,3-dibutyl-4-[[2'-(1H-tetrazol -5-yl)[1,1'-biphenyl]-4-yl]methyl]-1H-pyrazole-5-carboxylic acid.

40. A method according to claim 31 wherein the compound of formula (I) is 3-butyl -1-(2-cyclopropylmethyl)-4-[[2'-1H-tetrazol-5-yl)[1,1'-biphenyl]-4-yl]methyl]-1H-pyrazole-5-carboxylic acid.

* * * * *